US011278593B2

(12) United States Patent
Campbell et al.

(10) Patent No.: US 11,278,593 B2
(45) Date of Patent: Mar. 22, 2022

(54) COMPOSITION AND METHODS FOR THE TREATMENT OF DEGENERATIVE RETINAL CONDITIONS

(71) Applicant: The Provost, Fellows, Foundation Scholars, and the other members of Board, of the College of the Holy and Undivided Trinity of Queen Elizabeth Near Dublin, Dublin (IE)

(72) Inventors: Matthew Campbell, Dublin (IE); Peter Humphries, Dublin (IE); Marian Humphries, Dublin (IE); Anna-Sophia Kiang, Bray (IE); Sarah Doyle, Dublin (IE); Luke O'Neill, Dublin (IE)

(73) Assignee: THE PROVOST, FELLOWS, FOUNDATION SCHOLARS, AND THE AND THE OTHER MEMBERS OF BOARD, OF THE COLLEGE OF THE HOLY AND UNDIVIDED TRINITY OF QUEEN ELIZABETH NEAR DUBLIN, Dublin (IE)

( * ) Notice: Subject to any disclaimer, the term of this patent is extended or adjusted under 35 U.S.C. 154(b) by 0 days.

(21) Appl. No.: 16/401,787

(22) Filed: May 2, 2019

(65) Prior Publication Data

US 2019/0314454 A1 Oct. 17, 2019

Related U.S. Application Data

(63) Continuation of application No. 14/347,806, filed as application No. PCT/EP2021/069333 on Oct. 1, 2012, now abandoned.

(30) Foreign Application Priority Data

Sep. 29, 2011 (GB) .................................... 1116815
Mar. 23, 2012 (GB) .................................... 1205131

(51) Int. Cl.
*A61K 38/20* (2006.01)
(52) U.S. Cl.
CPC .................................. *A61K 38/20* (2013.01)
(58) Field of Classification Search
CPC .................................................... A61K 38/20
See application file for complete search history.

(56) References Cited

U.S. PATENT DOCUMENTS

2007/0196336 A1* 8/2007 Todo ...................... C12N 15/86
424/93.2

FOREIGN PATENT DOCUMENTS

EP         2554662 A1    2/2013
WO    2006119128 A2   11/2006

OTHER PUBLICATIONS

Marneros. NLRP3 inflammasome blockade inhibits VEGF-A induced age-related macular degeneration. Cell Rep. 2013; 4(5):17) (Year: 2013).*
Qiao et al. Interleukin-18 regulates pathological intraocular neovascularization. Journal of Leukocyte Biology, 81:1012-1021; 2007 (Year: 2007).*
Tarallo et al. DICER1 Loss and Alu RNA Induce Age-Related Macular Degeneration via the NLRP3 Inflammasome and MyD88. Cell, 2012; 149(4):847-859.
Doyle et al. NLRP3 has a protective role in age-related macular degeneration through the induction of IL-18 by drusen components. Nature Medincine, May 2012;18(5):791-8.
Marneros. NLRP3 inflammasome blockade inhibits VEGF-A-induced age-related macular degeneration. Cell Reports, 2013;4:945-958.
Zarbin. Cell-Based Therapy for Degenerative Retinal Disease. zTrends in Molecular Medicine, 2016; 22(2):115-134.
Hirano et al. IL-18 is not therapeutic for neovascular age-related macular degeneration. Nature Medicine, 2014;20:1372-1375.
Campbell et al. IL-18: a new player in immunotherapy for agerelated macular degeneration?. Expert Rev. Clin. Immunol., 2014; 10(10), 1273-1275.
Doyle et al. IL-18 Attenuates Experimental Choroidal Neovascularization as a Potential Therapy for Wet Age-Related Macular Degeneration. Science Translational Medicine, 2014; 6(230):230ra44.
Ijima et al. "Interleukin-18 Induces Retinal Pigment Epithelium Degeneration in Mice" Invest Ophthalmol Vis Sci. Sep. 18, 2014; 55(10):6673-8 (Year: 2014).
Chen et al. Nature Medicine, 2012; 18(5), 658-660 (Year: 2012).
Doyle et al. Nature Medicine, May 2012; 18(5):791-8 (Year: 2012).
International Search Report and Written Opinion received in Corresponding PCT/EP2012/069333 dated Jan. 25, 2013.
Qiao, et al., "Interleukin-18 regulates pathological intraocular neovascularization", Department of Ophthalmology, Graduate School of Medicine, Kyushu University, Fukuoka, Japan, Journal of Leukocyte Biology, vol. 81, Apr. 2007, pp. 1012-1021.
UKIPO Search Report received in Application No. GB1116815.0 dated Jan. 12, 2012.

(Continued)

*Primary Examiner* — Vanessa L. Ford
*Assistant Examiner* — Sandra E Dillahunt
(74) *Attorney, Agent, or Firm* — McBee Moore & Vanik IP, LLC

(57) ABSTRACT

The present invention is directed to compositions and methods for the treatment of degenerative retinal conditions. According to a general aspect, the present invention is directed to inflammatory mediators, preferably components or substrates of the NLRP3-inflammasome, for use in the treatment of degenerative retinal conditions involving drusen and anaphylatoxin-induced choroidal-neovascularisation. The invention is also directed to a method for the treatment of degenerative retinal conditions involving drusen and anaphylatoxin-induced choroidal-neovascularisation and to recombinant vectors and recombinant proteins for use in such methods. The present invention also provides a method for determining the risk of developing or monitoring the progression of diseases involving drusen and anaphylatoxin-induced choroidal neo-vascularisation.

13 Claims, 20 Drawing Sheets

(56) References Cited

OTHER PUBLICATIONS

Park, et al., "Evidence of IL-18 as a Novel Angiogenic Mediator", The American Association of Immunologists, The Journal of Immunology, 2001, pp. 1644-1653.

Kim, et al., "Application of Plasmid DNA Encoding IL-18 Diminishes Development of Herpetic Stromal Keratitis by Antiangiogenic Effects", The American Association of Immunologists, Inc., The Journal of Immunology, Antiangiogenic Effects of IL-18, pp. 510-516.

* cited by examiner

COMPOSITION AND METHODS FOR THE TREATMENT OF DEGENERATIVE RETINAL CONDITIONS

CROSS REFERENCE TO RELATED APPLICATIONS

This application is a continuation of U.S. patent application Ser. No. 14/347,806, filed 27 Mar. 2014, which is a § 371 National Stage Application of PCT/EP2012/069333, filed Oct. 1, 2012, which claims priority to GB 1116815.0, filed Sep. 29, 2011 and GB 1205131.4, filed Mar. 23, 2012. The disclosures of the priority applications are incorporated in their entirety herein by reference.

BACKGROUND

Field of the Invention

The present invention is directed to compositions and methods for the treatment of degenerative retinal conditions.

Specifically, the present invention is directed to compositions and methods for treating degenerative retinal conditions involving the drusen and anaphylatoxin-induced choroidal neo-vascularisation and to the use of gene delivery vectors which direct the expression of selected gene products, including inflammatory mediators, components or substrates of the NLRP3-inflammasome, suitable for treating or preventing degenerative retinal conditions involving the drusen and anaphylatoxin-induced choroidal neo-vascularisation, including pathologically-induced CNV. Preferably, the degenerative retinal conditions involving the drusen and anaphylatoxin-induced choroidal neo-vascularisation is age-related macular degeneration.

Description of Related Art

In the developed world, age-related macular degeneration (AMD) is the most prevalent cause of legal blindness in older individuals. AMD is a progressive disease, characterized by the accumulation of focal extracellular deposits on Bruch's membrane below the retinal pigment epithelium (RPE) in the macula, which is recognized in an eye examination as drusen. Drusen accumulation is the major pathological hallmark common to both dry and wet AMD. The presence of drusen in the macula, the density of the deposits and the area covered by this material represent early stages in the AMD disease process. Individuals with drusen are considered at risk for progressing to the end-stage blinding forms of AMD. Geographic atrophy (GA), the end stage of the atrophic "dry" form of AMD, culminates in vision loss following focal degeneration of the RPE below the fovea. Without the RPE, the foveal cone photoreceptors degenerate, causing central retinal blindness. Choroidal neovascularization (CNV) characterizes the end stage of the exudative "wet" form of AMD, with new blood vessels breaking through Bruch's membrane/RPE that hemorrhage, causing a blood clot to form between the RPE and foveal photoreceptors resulting in immediate blindness.

The disease, AMD, is classically multi-factorial, with both environmental and genetic factors involved. Sequence variants associated with disease susceptibility have now been characterized in a growing number of immune regulated genes. Activation of complement on ocular surfaces is thought to play a major role in the early disease process, resulting in drusen deposition. However, the mechanisms involved in the initiation of the inflammatory responses observed in the eyes of AMD subjects are still unresolved.

Drusen deposits are particulate protein aggregates, extracellular in nature, characteristics of known activators of the sterile inflammatory response mediated by NACHT, LRR and PYD domains-containing protein 3 (NLRP3). NLRP3 acts as a receptor for "danger" signals such as ATP, uric acid crystals, amyloid-like structures and mitochondrial dysfunction, which activate the inflammasome comprising NLRP3, Apoptosis-associated Speck-like domain containing a Caspase-recruitment domain (ASC) and pro-caspase-1 and resulting in the cleavage of pro-IL-1β and pro-IL-18, into their mature pro-inflammatory forms. Furthermore, excessive drusen accumulation can disrupt the adjacent RPE cells which subsequently die by necrosis a cellular process now known to activate the NLRP3 inflammasome.

Current antibody-based therapies target advanced forms of AMD by inhibiting the bioactivity of VEGF. However, direct and regular intraocular injection of these monoclonal antibodies (Lucentis® and Avastin®) carry the risk of retinal detachment, haemorrhage and infection. No FDA-approved treatments are available for dry macular degeneration, although a few now are in clinical trials. Thus, the generation of new AMD therapies is important commercially.

From a clinical perspective, while inflammatory processes have long been associated with AMD pathology and disease development, we suggest that global inhibition of inflammation in the retina in the case of wet AMD would not be a sound therapy. Lending strength to our observations, the results of recent clinical trials of Infliximab (Remicade®) in individuals with wet AMD showed that in more than 50% of these subjects, symptoms were greatly exacerbated.

IL-18 is a molecule with a wide-ranging variety of functions, many of which are dichotomous opposites of each other depending on the environment in which IL-18 is released. This is the case with regards to the role of IL-18 in regulating angiogenesis or blood vessel growth. For example, IL-18 has been shown to have a pro-angiogenic effect in a model of rheumatoid arthritis (Park et al, 2001, Evidence of IL-18 as a novel angiogenic mediator. Journal of Immunology 167: 1644-1653) whereas it has been shown to be anti-angiogenic in herpetic stromal keratitis (Kim B et al, 2006, Application of plasmid DNA encoding IL-18 diminishes development of herpetic stromal keratitis by antiangiogenic effects. Journal of Immunology 175:509-516). The reason for the discrepancy between the role of IL-18 as an angiogenic agent versus its role as an angiostatic agent remains unclear but is in part determined by the specific vascular beds involved.

Qiao et al (Interleukin-18 Regulates Pathological Intraocular Neovascularaization. Journal of Leukocyte Biology. Volume 81, April 2007, 1012-1021) uses an oxygen-induced model of retinopathy of prematurity, which triggers the development of intraocular neovascularization. Intraocular neovascularization involves neovascularization of the blood vessel lining the inner retina. Qiao et al administered recombinant IL-18 to C57BL/6 mice during the development of oxygen induced retinopathy, and found no inhibition of neovascularization. Qiao et al concluded that IL-18 regulates intraocular retinal neovascularization by promoting its regression rather than inhibiting its development.

SUMMARY

The present invention is directed to a new and improved therapy for degenerative retinal conditions involving the drusen and anaphylatoxin-induced choroidal neo-vascularisation and/or pathologically-induced CNV, preferably choroidal neo-vascularisation associated with AMD, more preferably wet AMD.

The choroid is a vascular bed which is extraoccular and completely separate to the retina. It does not act in the same way as the retinal intraocular vasculature. Choroidal neovascularization (CNV) is the creation of new blood vessels in the choroid layer of the eye. This is a common symptom of the degenerative maculopathy wet AMD (age-related macular degeneration) and is distinct from retinal neovascularization (intraocular) of Qiao et al.

In this specification, the term choroidal neo-vascularisation (CNV) ideally does not encompass retinal neovascularization (intraocular). Intraocular neovascularization involves neovascularization of the blood vessel lining the inner retina. This is distinct to choroidal neovascularization which involves the choroids, a vascular bed which is extraoccular and completely separate to the retina. Ideally, in this specification the use of IL-18 for intraocular neovascularization is excluded.

In this specification, the term "NLRP3 inflammasome, component or substrate" will be understood to cover NALP3, ASC and pro-caspase-1 and pro-IL-18 and IL-18. When NLRP3, ASC and pro-caspase-1 oligomerise they produce active caspase-1 which then cleaves pro-IL18 to mature Il-18. Thus, pro-IL18 is a component of the inflammasome by virtue of the fact that it is a substrate of caspase-1. The 24 KDa inactive precursor of IL-18 is referred to as "pro-IL-18" and 18 KDa mature IL-18 is referred to as "IL-18" "or pro-inflammatory IL-18". NLRP3 and NALP3 are used interchangeably in this specification and refer to the same inflammasome component. In a preferred embodiment, the NLRP3 inflammasome, component or substrate is mature Il-18, referred to as "Il-18". It will be understood that reference to IL-18 also means the nucleotide sequence defined by NCBI Accession no. NM_001562.3 and the protein sequence defined by NCBI Accession no. NP_001553.1. It will also be understood that reference to delivery of IL-18 also covers the delivery of recombinant IL-18 (rIL-18), for example locally via intraocular injection or systemically via intravenous injection.

We have shown that drusen isolated from donor AMD eyes activates the NLRP3-inflammasome, causing secretion of IL-1β and IL-18. Drusen component C1Q, also activates the NLRP3-inflammasome. Moreover, oxidative-stress related protein-modification carboxyethyl-pyrrole (CEP), a biomarker of AMD primes the inflammasome. We have found that cleaved caspase-1 and NLRP3 in activated macrophages in the retina of CEP-MSA-immunised mice, which models a dry AMD-like pathology. We show that laser induced choroidal-neovascularisation (CNV), an accepted animal model of wet AMD, is exacerbated in Nlrp3$^{-/-}$, but not Il1r1$^{-/-}$ mice, directly implicating IL-18 in regulating CNV development. These findings are indicative of a protective role for NLRP3 and IL-18 in the progression of AMD.

It is our opinion that NLRP3 and it's components are directly implicated as a protective agent against the major disease pathology of AMD. Thus, strategies aimed at producing or delivering IL-18 to the eye, may prove beneficial in preventing the progression of CNV, especially in the context of wet AMD.

DETAILED DESCRIPTION OF A PREFERRED EMBODIMENT

According to a first general aspect of the invention, there are provided inflammatory mediators, preferably components or substrates of the NLRP3-inflammasome, for use in the treatment of degenerative retinal conditions involving the drusen and anaphylatoxin-induced choroidal-neovascularisation.

Retinal (intraocular) neovascularization and choroidal (extraocular) neovascularization of the present invention are distinct conditions of the vasculature. We have found that IL-18 suppresses the promotion of choroidal neovascularisation.

Ideally, the components or substrates of the NLRP3-inflammasome is IL-18, including recombinant IL-18.

Ideally, the retinal condition includes pathologically-induced CNV, such as choroidal-neovascularisation (CNV) associated with AMD, preferably dry and/or wet AMD, more preferably wet AMD.

According to this general aspect of the invention, the inflammatory mediators, components or substrates may be used in controlling, maintaining or stimulating Interleukin-18 (IL-18) expression in a subject at risk of developing age-related macular degeneration and prevent the progression of CNV, especially in the context of wet AMD.

It will be understood that up-stream components of the inflammasome may also be used. These components include NLRP3, ASC or pro-caspase-1, pro-IL-18 etc. However, delivery of IL-18 or recombinant IL-18 is preferred.

Ideally, the inflammatory mediators, components or substrates, including Interleukin-18 (IL-18) are administered prior to the development of neo-vascular disease or in early-stage neo-vascular disease.

Activation of the NLRP3 inflammasome by drusen suggest that a balance may exist, whereby a certain focal level of drusen is tolerated due to its ability to induce IL-18 which in turn may act as an anti-angiogenic effector, maintaining choroidal homeostasis in an inflammatory micro-environment. It is likely that once a critical level of drusen accumulates, its protective role is negated by excessive damage to the surrounding tissues. Importantly, we have demonstrated that drusen-inducible inflammatory mediators are protective against CNV development and that it is the resultant NLRP3 mediated elevation of IL-18 that prevents the downstream production of VEGF. Moreover, IL-18 has been shown not to play a role in the development of experimental uveitis, a more conventional model of inflammation.

According to one embodiment the degenerative retinal condition is age-related macular degeneration. It will be understood that the age-related macular degeneration referred through throughout may be wet age-related macular degeneration or dry age-related macular degeneration.

According to a preferred embodiment of the invention, there is provided Interleukin-18 (Il-18) or recombinant IL-18 for use in controlling choroidal-neovascularisation (CNV) in a patient at risk of developing wet age-related macular degeneration (AMD). The resultant NLRP3 mediated elevation of IL-18 prevents the downstream production of VEGF which we have found is protective against CNV development.

All references to IL-18 herein should be understood to also refer to recombinant IL-18 (rIL-18).

According to a general aspect of the invention, IL-18 or recombinant IL-18 may be administered to result in and provide a local effect or a systemic effect.

IL-18 or recombinant IL-18 protein may be administered per se. IL-18 or recombinant IL-18 may also be administered in the form of a pharmaceutical composition. Optionally, IL-18 may be administered with a pharmaceutically acceptable adjuvant. Such adjuvants may include carriers, diluents, and excipients such as sterile water and oil. Further adjuvants, excipients and auxiliary substances are listed below.

It will be understood that administration may be carried out via a variety of routes. These routes are designed to provide a local or systemic effect as required. These routes include, but are not limited to, oral, topical, pulmonary, rectal, subcutaneous, intradermal, intranasal, intracranial, intramuscular, intraocular, or intra-articular injection, and the like. The most typical route of administration is intravenous followed by subcutaneous, although other routes can be equally effective. Intramuscular injection can also be performed in the arm or leg muscles.

In some methods, IL-18 may be injected directly into a particular tissue. In other embodiments, administration may be as part of a sustained-release composition.

For parenteral administration, IL-18 may be administered as injectable dosages of a solution or suspension of the substance in a physiologically acceptable diluent with a pharmaceutical carrier that can be a sterile liquid such as water, oils, saline, glycerol, or ethanol. Additionally, auxiliary substances, such as—wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are suitable liquid carriers, particularly for injectable solutions.

IL-18 can also be administered in the form of a depot injection or implant preparation which can be formulated in such a manner as to permit a sustained-release of the protein IL-18.

Typically, compositions may be prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced delivery.

Oral formulations may take the form of solutions, suspensions, tablets, pills, capsules, sustained-release formulations or powders. Topical application can result in transdermal or intradermal delivery. Alternatively, transdermal delivery can be achieved using a skin patch.

Ideally, the above administration modes result in delivery of IL-18 to the eye, preferably to the retina, more preferably to the choroid layer.

According to a preferred embodiment of the invention, local delivery means include direct injection of IL-18, rIL-18 or pharmaceutical composition comprising IL-18/rIL-18, to the eye, such as intra-ocular injection. Injections may be sub-retinal, made into the vitreous of the eye (intra-vitreal), behind the eye (retrobulbar), below the conjunctiva (subconjunctival) or under tenon's capsule (subtenons).

According to another preferred embodiment, pro-inflammatory Interleukin-18 (IL-18), rIL-18 or pharmaceutical composition comprising IL-18/rIL-18, may be delivered to the subject systemically. Systemic delivery means may include parenteral or enteral means and essentially encompass all non-local delivery means. Ideally, systemic delivery means include injection, direct injection, and/or viral mediated delivery.

According to a preferred embodiment, systemic injection techniques include intravenous delivery by intravenous injection. Intravenous injection may be to a peripheral vein of the subject. For this administration route, IL-18, rIL-18 or a pharmaceutical composition comprising IL-18/rIL-18 is adminstered/injected directly into the blood stream of the subject.

Preferably, IL-18 is delivered to the retina systemically, by direct injection, such as intravenous injection and/or by viral mediated delivery.

Viral mediated delivery techniques include adeno-associated virus (AAV), adenovirus or lentivirus gene delivery vector. Optionally, viral mediated delivery techniques, including AAV therapy, may be applied up-stream of inflammasome components by introducing NLRP3, ASC or pro-caspase-1.

According to another preferred embodiment of the invention, there is provided a recombinant viral gene delivery vector which directs the expression of pro-IL-18 or IL-18 in a form suitable for the treatment of choroidal, neo-vascularisation.

The recombinant viral gene delivery vector may be in a form for administration systemically, for example by intravenous administration.

The recombinant viral gene delivery vector may also be in a form for administration to the eye of a subject at risk of developing AMD, preferably wet AMD.

For example, the vector may be in a form suitable for delivery to the eye via intraocular injection, including sub-retinal or intra-vitreal injection.

The viral vector may be an adeno-associated virus (AAV), adenovirus or lentivirus gene delivery vector. Ideally, delivery of the gene delivery vector is via sub-retinal injection where, for example, a small amount of fluid is injected underneath the retina. This has an advantage in term of long term disease management following a single administration. The vector may also be optimized for intra-vitreal administration in subjects.

According to a most preferred embodiment of the invention, there is provided a new gene therapy for degenerative retinal conditions involving the drusen and anaphylatoxin-induced choroidal-neovascularisation, preferably wet AMD, involving the use of viral, preferably AAV, mediated delivery of IL-18 to a subject to control, maintain or stimulate Interleukin-18 (IL-18) expression in a subject at risk of developing a degenerative retinal conditions involving the drusen and anaphylatoxin-induced choroidal-neovascularisation, such as age-related macular degeneration (AMD).

According to this preferred embodiment, there is provided a recombinant adeno-associated virus (AAV) gene delivery vector which directs the expression of IL-18 suitable for administration to the eye of a subject at risk of developing AMD, preferably wet AMD.

The AAV vector comprises nucleotides encoding Il-18 gene. The AAV may be any one of AAV serotype 1 to 11, preferably serotypes 2, 8 or 9. Ideally, the IL-18 gene is flanked by AAV inverted terminal repeats (ITR).

Many different promoters may be used. These are ideally cell specific promoters. These may include, retinal pigment epithelial cell (RPE) specific promoters such as CRALBP or RPE65, endothelial cell specific promoters such as Tie-2 or claudin-5, or photoreceptor specific promoter including rhodopsin.

AAV is the main viral vector used for eye diseases as it is very efficient at transducing retinal cells. It is also non-immunogenic which is very important from a clinical point of view. AAV technology has emerged as a very safe means of delivering genes to host tissue, especially tissues of the central nervous system such as the retina. In contrast to adenoviruses which can integrate into the host genome, AAVs will infect cells and subsequently their genetic material will reside in the nucleus as episomal DNA. This factor is likely key to their excellent safety profile and low immunogenicity. In tandem, AAV technology is now being used in a range of clinical trials for Parkinson's disease, Alzheimer's disease and muscular dystrophy and in relation to this proposal, AAVs are now well established for retinal use, with numerous clinical trials on-going for the treatment of the recessive form of Retinitis pigmentosa termed Leber's Congenital Amaurosis (LCA).

To date, 11 AAV serotypes have been described in the literature and the key differences in these serotypes relates to the target cells that they can infect. AAV-2, AAV-8 and AAV-9 have been found to transduce RPE cells effectively. Thus, the present invention may preferably involve the use of AAV-2, AAV-8 and/or AAV-9.

According to one preferred embodiment, the invention involves constructing a vector (e.g. AAV vector such as AAV serotypes −2, −8 and −9) by cloning a gene encoding IL18 including 5' and 3' UTRs and introducing this gene into a vector such as to incorporate left and right AAV inverted terminal repeats (L-ITR and R-ITR).

According to a second aspect of the invention, there is provided a method of treating degenerative retinal conditions involving drusen and anaphylatoxin-induced choroidal-neovascularisation comprising administering inflammatory mediators, components or substrates of the NLRP3-inflammasome to a subject in need of treatment.

According to a preferred embodiment, there is provided a method for treating wet age-related macular degeneration (AMD) comprising administering Interleukin-18 (Il-18) to a subject at risk of developing age-related macular degeneration. IL-18 may be administered to provide a local or systemic effect.

According to a preferred embodiment, local delivery means include direct intra-ocular injection. Injections may be sub-retinal, made into the vitreous of the eye (intravitreal), behind the eye (retrobulbar), below the conjunctiva (subconjunctival) or under tenon's capsule (subtenons).

According to another preferred embodiment, pro-inflammatory Interleukin-18 (IL-18) may be delivered to the subject systemically. Systemic delivery means may include parenteral or enteral means and essentially encompass all non-local delivery means. Ideally, systemic delivery means include injection, direct injection, and/or viral mediated delivery. According to a most preferred embodiment, systemic injection techniques include intravenous delivery by intravenous injection. Intravenous injection may be to a peripheral vein of the subject. For this administration route, recombinant IL-18 is adminstered/injected directly into the blood stream of the subject.

According to a third aspect of the invention, there is provided the use of NLRP3-Inflammasome induced mediators, preferably pro-inflammatory IL-18 (Il-18), as a biomarker to indicate the risk of developing diseases involving drusen and anaphylatoxin-induced choroidal neo-vascularisation, such as wet or dry age-related macular degeneration.

According to a fourth aspect of the invention, there is provided a method for determining the risk of developing or monitoring the progression of diseases involving drusen and anaphylatoxin-induced choroidal neo-vascularisation, such as wet or dry age-related macular degeneration, in a subject, using inflammasome induced mediators, preferably pro-inflammatory IL-18 (IL-18), as a biomarker the method comprising:

obtaining the level of circulating IL-18 and/or IL-18 binding protein levels in a subject;

comparing the level of IL-18 and/or IL-18 binding protein levels to a reference, wherein the subject's risk of development or progression of the disease drusen and anaphylatoxin-induced choroidal-neovascularisation is based upon the level of IL-18 levels and/or IL-18 binding protein in comparison to a reference.

It will be understood that the ratio of IL-18 and its binding protein (IL-18 binding protein) is conventionally used as a measure of variation from the normal reference, although IL-18 levels may be used alone.

BRIEF DESCRIPTION OF THE DRAWINGS

The invention will now be described in relation to the following non-limiting figures and examples.

MATERIALS & METHODS

Drusen Isolation

Drusen and minor amounts of Bruch's membrane were isolated as previously described (8) from six AMD donor eyes (88M, 91F, 97M, 85F, 85M and 80M) for use in these experiments.

CEP-Albumin Production

Human Serum Albumin (Sigma Aldrich, USA) was adducted with CEP as previously described (54).

ELISA Analysis

ELISA's were used to quantify cytokines in supernatants from the various experimental groups used throughout this study. IL-1β (RnD Systems), IL-18 (MBL International), IL-6 (RnD Systems), TNF-α (RnD Systems) and VEGF (RnD Systems) were analyzed throughout. All ELISA's were conducted a minimum of 3 times in triplicate. Inhibitors used during this study were added at the following highest concentrations 1 h prior to inflammasome activation: 1 μg/ml of caspase-1 inhibitor VI (Calbiochem), 5 μM cytochalasin D (Sigma Aldrich, Ireland), 10 μM CA-074 Me (cathepsin B inhibitor) (Sigma Aldrich, Ireland), 10 μM DPI (Sigma Aldrich, Ireland).

Western Blot Analysis

Generally, antibodies specific for caspase-1 (Santa-Cruz Biotech), beta-actin (Abcam), NLRP3 (Sigma Aldrich, Ireland), TLR-4 (Santa-Cruz Biotech) were incubated on membranes overnight at 4° C. Membranes were washed with TBS, and incubated with a secondary antibody against rabbit (IgG) with Horse-Radish-Peroxidase (HRP) conjugates (1:2500) (Sigma-Aldrich, Ireland), or mouse (IgG) (1:1000), (Sigma-Aldrich, Ireland), for 3 hours at room temperature. Immune complexes were detected using enhanced chemiluminescence (ECL). All Western blots were repeated a minimum of 3 times.

Cell Culture

Figure 19:
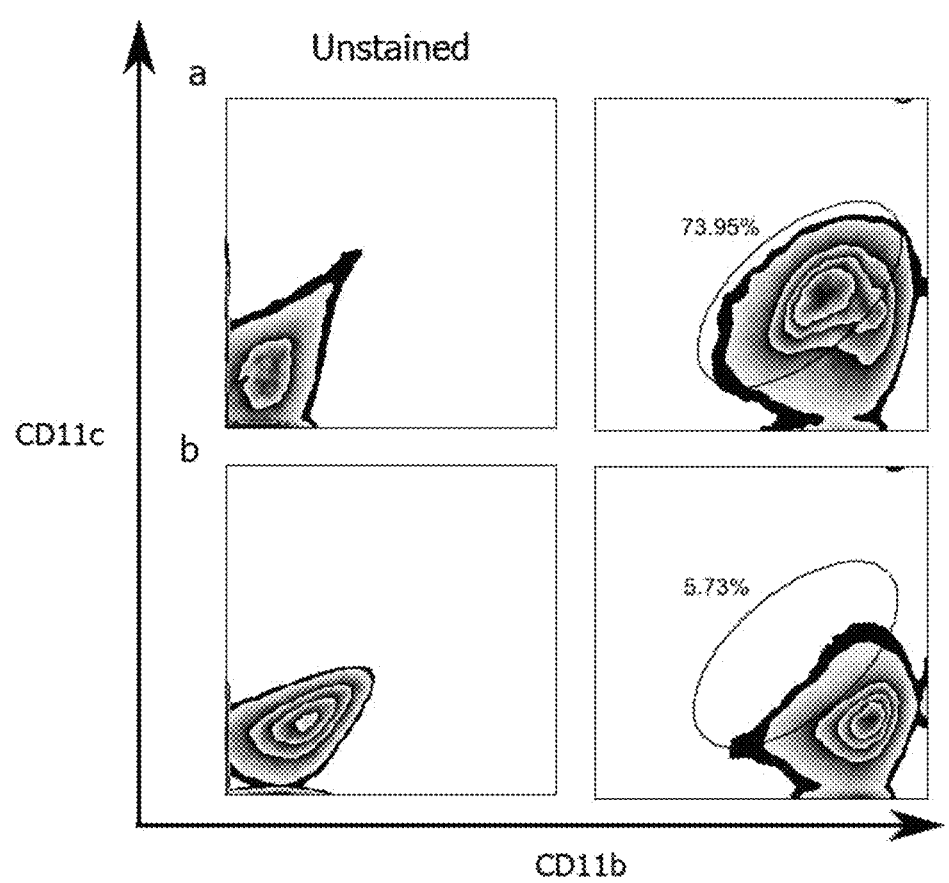
FIG. 19 Flow cytometry analysis of (a) BMDC's and (b) BMDM's stained for CD11c and CD11b.

ARPE-19 cell line (ATCC CRL 2302) were obtained from LGC promochem, THP1 cells and primary isolated human peripheral blood mononuclear monocytes (PBMCs) were used for in vitro inflammasome activation assays. Cells were cultured at 37° C., 5% $CO_2$, 95% air in a 1:1 mixture of Dulbecco's modified Eagle's medium (DMEM) and Ham's F12 medium with 1.2 g/L sodium bicarbonate, 2.5 mM L-glutamine, 15 mM HEPES, 0.5 mM sodium pyruvate (Sigma Aldrich) with 10% foetal calf serum (FCS). BMDCs and BMDMs were also isolated from WT, NLRP3−/−, TLR-2−/−, C3H/HeN and C3H/HeJ mice on a congenic C57/Bl6 background. BMDCs and BMDMs were stained with anti-CD11c-APC and anti-CD11b-PeCy7. Cells were gated on live single cells and expression of CD11c and CD11 b was assesed by flow cytometry (FIG. 19). Mouse bEnd.3 microvascular endothelial cells were grown on fibronectin (Sigma Aldrich Ireland) coated tissue culture flasks in DMEM containing Glutamax and 10% FCS.

ASC Speck Formation Analysis.

Immortalized BMDMs (Gift from Dr Eicke Latz, University of Bonn) expressing yellow fluorescent (YFP) protein-labelled ASC were primed with LPS, HSA or CEP-HSA, then activated with drusen or C1Q for either 3 or 6 hrs respectively. Live cell imaging of speck formation was undertaken using a temperature and $CO_2$ regulated confocal laser scanning microscopy (Olympus FluoView™ FV1000).

CEP-MSA Immunization

We used standard mouse immunization protocols (55). We anesthetized mice with ketamine-xylazine in PBS (80-90 mg/kg ketamine, 2-10 mg/ml xylazine). We used 200 μg of CEP-MSA in CFA or IFA (Difco Labs) for initial and all booster doses as described previously (18).

Murine Models of Choroidal Neovascularisation (CNV)

Figure 20:
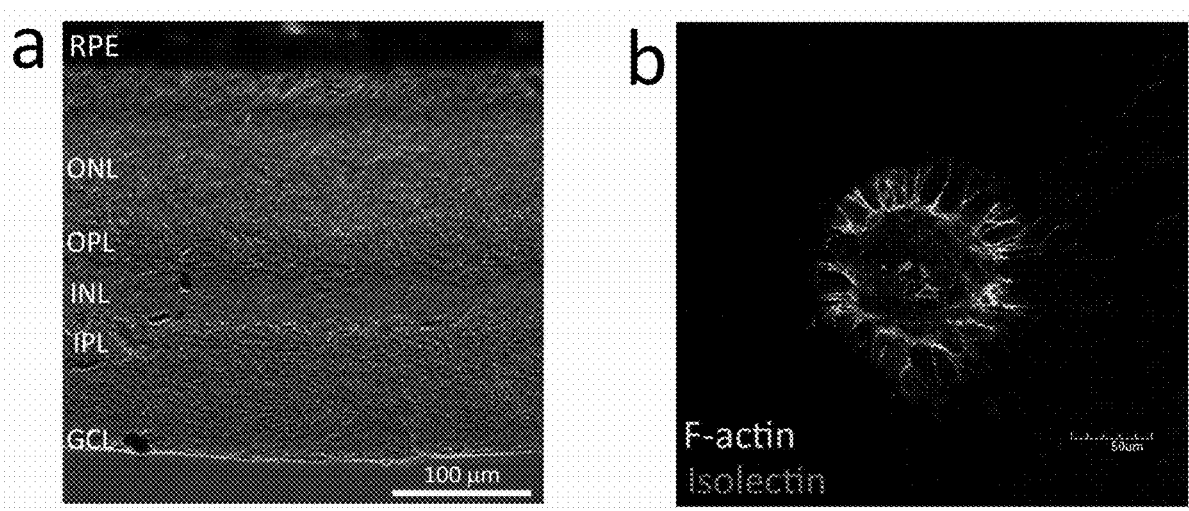
FIG. 20 (a) The RPE lies adjacent to the outer segments of the photoreceptors. (b) A targeted thermal disruption of the retina/RPE/Bruch's membrane/choroid complex with a 532 nm laser causing a 50 μm diameter injury, *Griffonia simplicifolia* isolectin-Alexa-568 (red) and Phalloidin-Alexa-488 (Green).

All animal experiments conducted during the course of this work adhered to the Association for Research in Vision and Ophthalmology (ARVO) standards and all relevant national and institutional approvals were obtained prior to commencement of the work. CNV, in which the vascular bed proliferates into the retina, mimicking neovascular AMD, was induced in mice using a green 532 nm Index Iris laser (532 nm, 140 mW, 100 mSec, 50 μm spot size, 3 spots per eye) incorporating a microscopic delivery system as described previously (21). This technique was used to induce CNV in Nlrp3−/−, Il1r1−/−, IL-18−/− and WT mice, and in each experimental assay animals were gender matched. In tandem, we also directly injected, intra-vitreally post laser burn, neutralizing antibodies directed against IL18 (Abcam). Mice were sacrificed 6 days post experiment and the neural retina was removed. Eye-cups were then incubated with a Griffonia-simplicifolia-isolectin-Aleax-568 molecule (Molecular Probes) (1:300) overnight at 4° C. and CNV's assessed by confocal microscopy (FIG. 20a,b).

Indirect Immunostaining of Retinal Flatmounts and Retinal Cryosections

Indirect immunostaining was used to analyse activated macrophages and cleaved caspase-1, present in the neural retina in the animal models of AMD. Antibodies against F4/80, CD68 (Abcam) for activated macrophages, and caspase-1 (P10) (Santa Cruz Biotech), NLRP3 (Santa Cruz Biotech and Abcam) and IL18 (Abcam) were used in conjunction with confocal laser scanning microscopy (Olympus FluoView™ FV1000).

Statistical Analyses

Statistical analysis was performed using Student's T-test, with significance represented by a P value of 50.05 when 2 individual experimental groups were being analysed. For multiple comparisons, as was the case in the ELISA analyses, ANOVA was used with a Tukey-Kramer post-test and significance represented by a P value of 50.05.

Results

The RPE is a monolayer of cuboidal cells located between the outer retina and choroid. This melanized neuroepithelium has numerous functions including a) the adsorption of scattered and reflected light, b) the formation of the outer blood-retinal barrier (oBRB) and c) the removal by phagocytosis of the effete tips of the photoreceptor outer segments (22). Proteomic and immunohistochemical analysis of drusen have identified virtually every protein involved in the complement cascade, proteins found in amyloid deposits as well as a number of crystallins, proteins synthesized in response to stress (23, 24). Considering the recent discovery that host-derived particulate matter such as cholesterol crystals and amyloid deposits (25, 26) can activate the NLRP3 inflammasome, we were interested to determine whether drusen could also initiate the activation of the inflammasome.

Drusen Activates the NLRP3 Inflammasome

Figure 1:
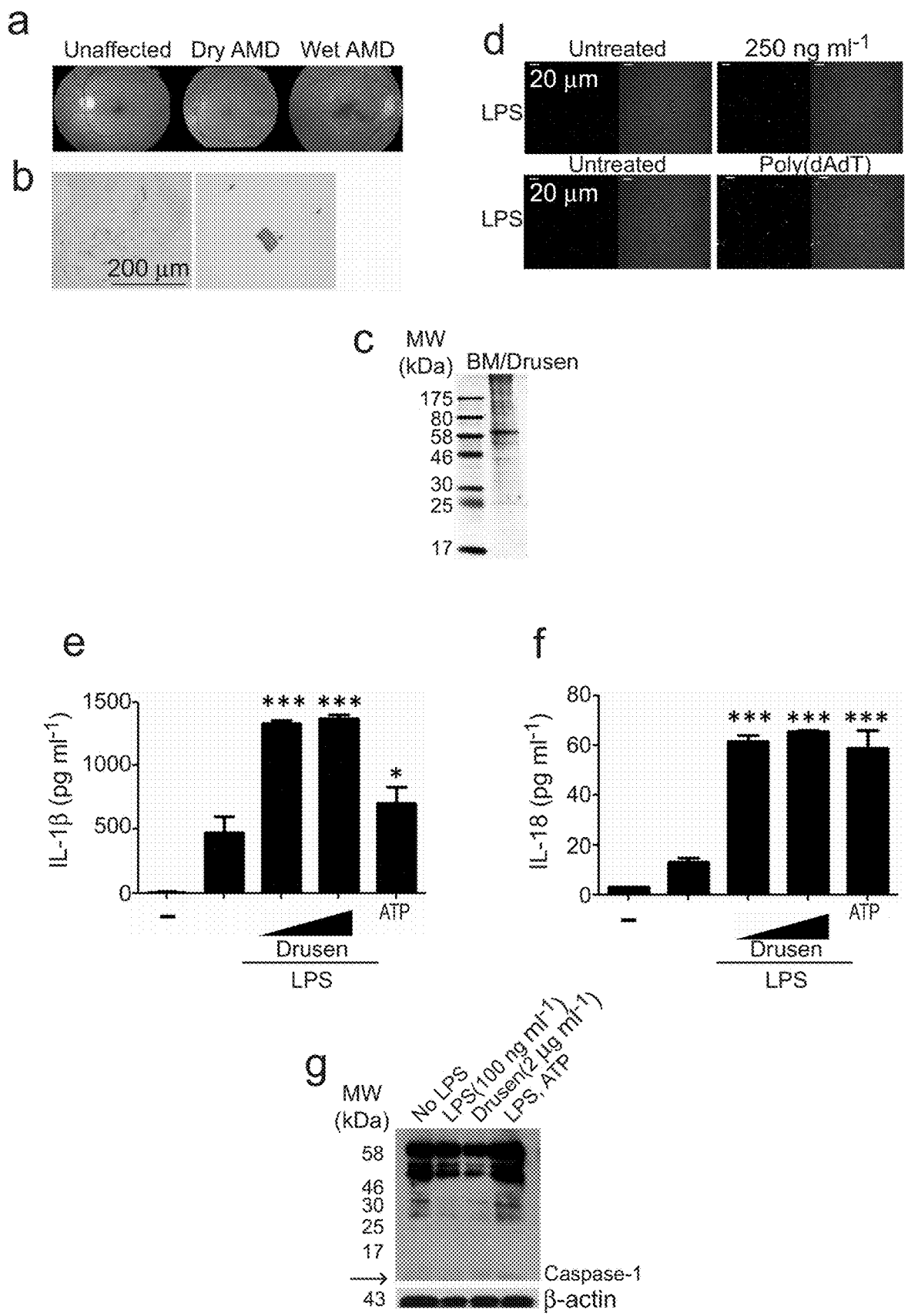
FIG. 1: Drusen activates the NLRP3 inflammasome: (a) Fundus photography from non-smoking un-affected, dry and wet AMD-affected individuals. (b) Drusen fragments in a range of sizes from just under 500 µm to sub-microscopic sized particles. (c) SDS-PAGE analysis of a Bruch's membrane (BM)/drusen preparation. (d) Live cell imaging of immortalised BL6 BMDMs stably expressing yellow-fluorescent protein labelled-ASC (YFP-ASC). Cells were primed for 3 hrs with LPS followed by treatment with 250 ng ml$^{-1}$ drusen for a further 2 hrs, Poly(dAdT) was used as a positive control. Oligomerisation of ASC-YFP was observed by speck formation, original magnification ×60. (e, f) Production of IL-1β and IL-18 was measured by ELISA in Human PBMC primed overnight with 100 ng ml$^{-1}$ LPS and subsequently treated for 7 hours with increasing doses of the drusen preparation (250 ng ml$^{-1}$ and 500 ng ml$^{-1}$) (*P≤0.0001). (g) Western Blot of cleavage products of caspase-1 following treatment of THP-1 cells with drusen. (h) Production of IL-1β (left hand panel) and IL-6 (right hand panel) as measured by ELISA in wild-type (WT) (blue bars) and NLRP3-deficient (Nlrp3$^{-/-}$) (red bars) bone marrow-derived macrophages (BMDM's) after treatment with increasing doses of drusen (*P≤0.0001) (i) Production of IL-1β (left hand panel) and TNF (right hand panel) as measured by ELISA in WT (blue bars) and Nlrp3$^{-/-}$ (red bars) bone marrow-derived dendritic cells (BMDC's) after treatment with increasing doses of drusen (***P≤0.0001). All ELISA data are representative of a minimum of 3 separate experiments carried out in triplicate.
Figure 1:
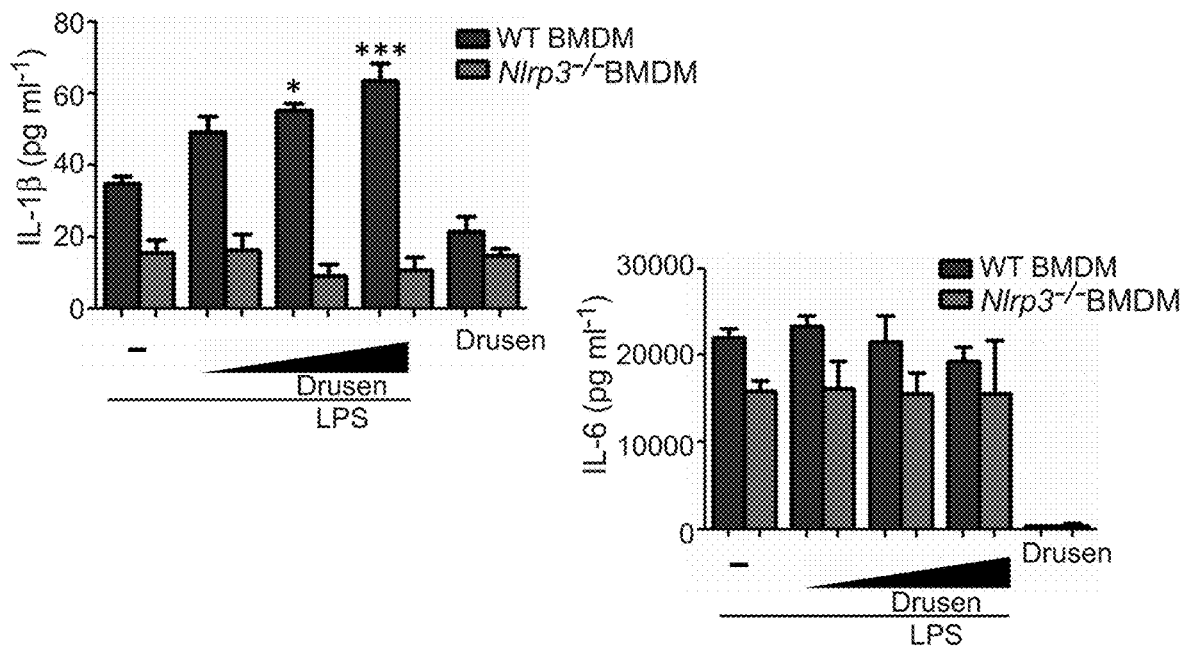
Figure 1:
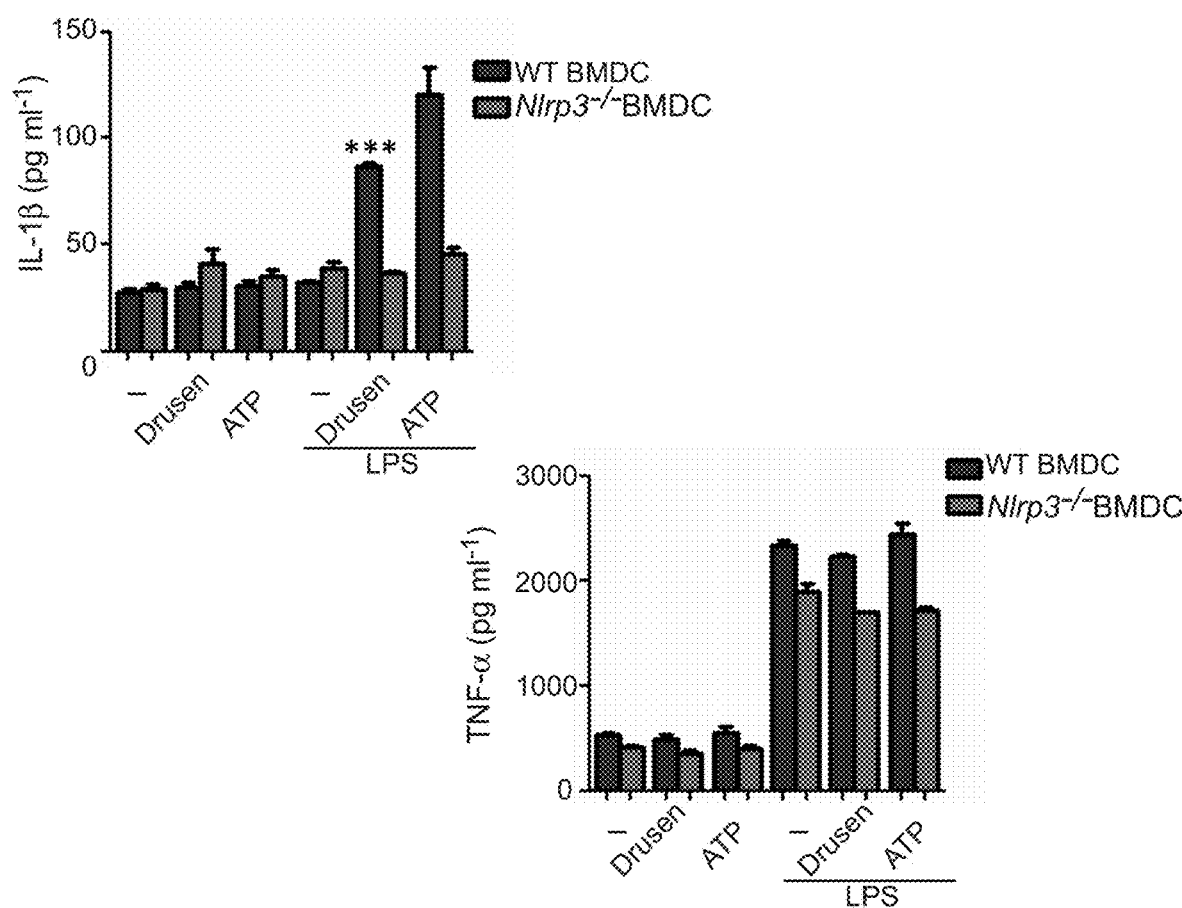

Fundus photography of an unaffected eye compared to those of individuals with either dry or wet AMD (FIG. 1a). Punctate light deposits in the fundus images represent drusen accumulation in both dry and wet AMD, with subretinal CNV apparent in the wet AMD photograph. Isolated drusen was sonicated in order to dissociate the sample into small particulate matter (FIG. 1b). SDS-PAGE analysis of the drusen sample showed a cohort of high molecular weight proteins greater than 60 kDa (FIG. 1c). The inflammasome is a multimeric protein complex. Caspase-1 is the cysteine protease activated in the inflammasome complex to cleave pro-IL-1β and pro-IL-18 into their mature forms. Activation of caspase-1 requires the protein ASC which forms oligomers creating a platform for the multimeric complex. Normally ASC is evenly distributed throughout the cell, but once activated ASC aggregates to a single point, known as a "speck". BMDMs that stably express a yellow fluorescent protein labelled-ASC (YFP-ASC) were primed with LPS and treated with drusen or transfected with Poly(dAdT) (positive control). ASC-YFP is difficult to discern in macrophages treated with LPS alone (FIG. 1d, left panels), however, in LPS primed macrophages activated with drusen, the formation of intense single fluorescent specks are clearly evident, indicative of ASC oligomerisation.

Figure 7:
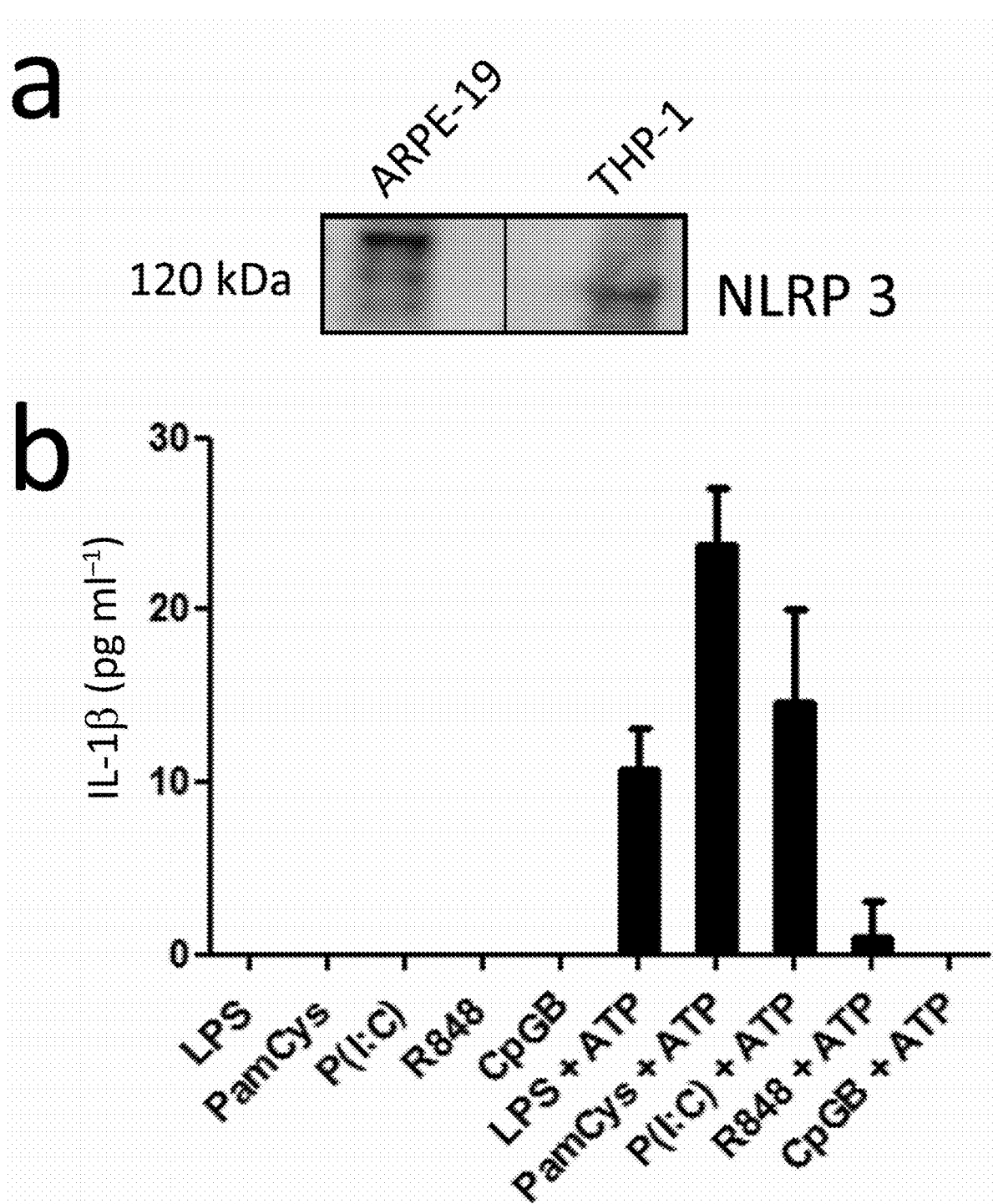
FIG. 7: (a) Western blot of NLRP3 expression in ARPE-19 cells (left side) and THP1 cells (right side), equal amounts of protein were loaded as determined by BCA assay. (b) ARPE-19 cells were primed with various TLR ligands; 100 ng/ml LPS, or 2 μg/ml Pam3Cys, or 25 μg/ml Poly(I:C), or 1 μg/ml R848, or 5 μg/ml CpG-ODN and either left un-treated or activated with ATP for a further hour. IL-1β production was then measured.
Figure 8:
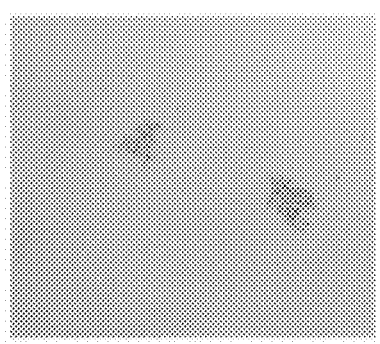
FIG. 8: a) RPE soup was observed under a light microscope to contain retinal/RPE material produced following isolation of drusen. b) This material (100 ng/ml, 250 ng/ml and 500 ng/ml) was added to LPS primed PBMCs but caused no increase in IL-1β levels, or c) IL-18 levels. d) IL-6 expression was un-changed with increasing doses of RPE soup. e) RPE soup elicited no change in IL-1β levels in WT or Nlrp3$^{-/-}$ mouse BMDCs. f) There were no differential changes in IL-6 expression between the experimental groups.
Figure 8:
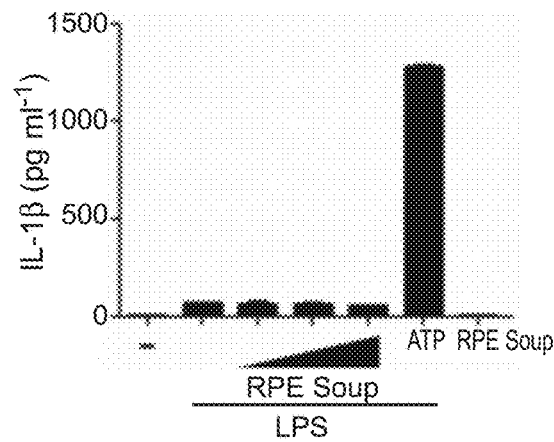
Figure 8:
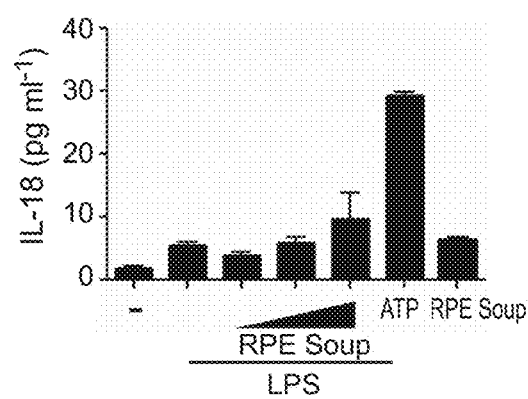
Figure 8:
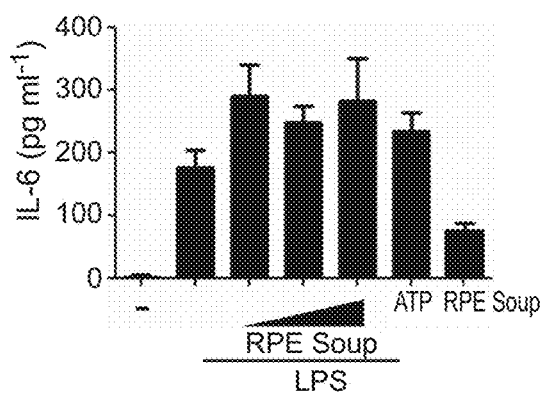
Figure 8:
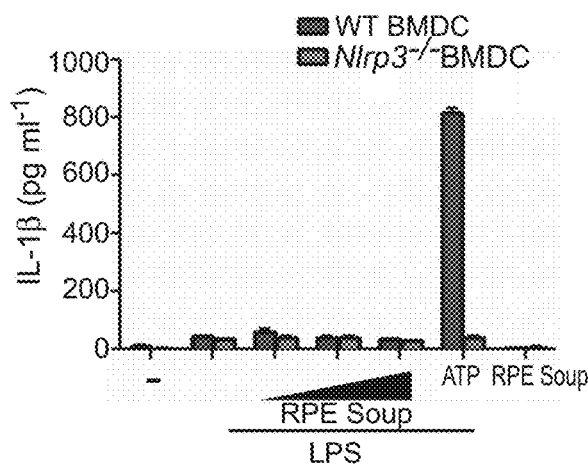
Figure 8:
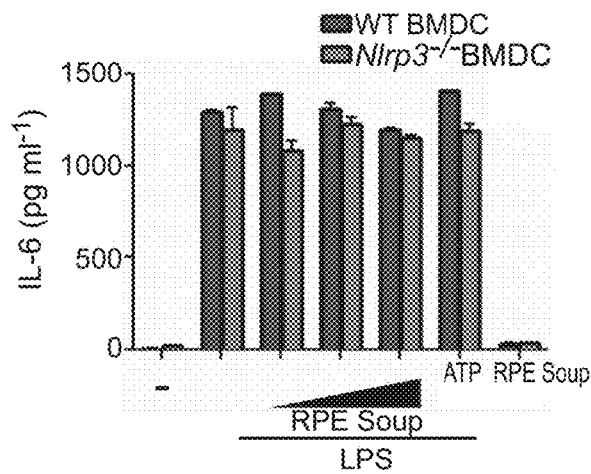
Figure 9:
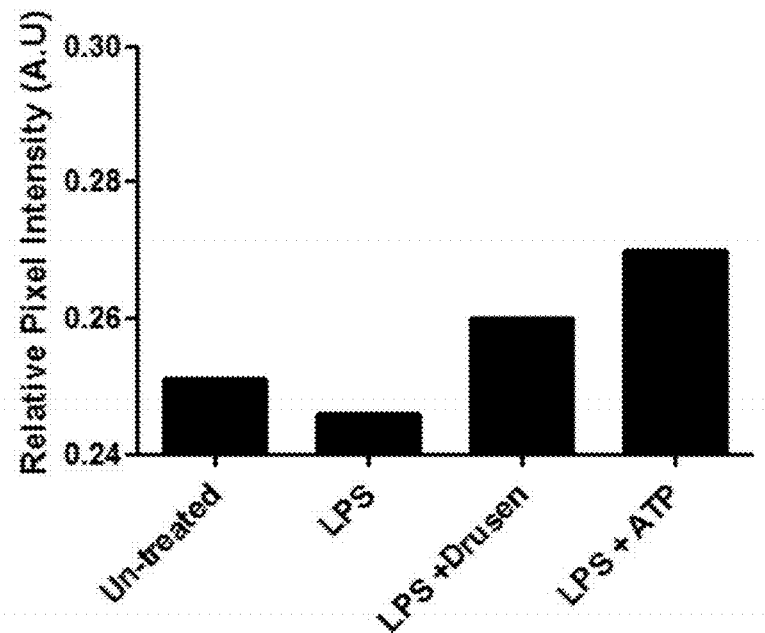
FIG. 9: Densitometric analysis of Caspase-1 P10 Western blot following treatment of THP1 cells with drusen.

It is thought that the inflammatory response associated with AMD has both a local and systemic component. We initially tested the ARPE-19 cell line for the presence of NLRP3 and for their ability to produce IL-1β in response to a range of TLR ligands and activation with ATP. We found that while ARPE-19 cells express NLRP3 the levels of IL-1β were at the lower limit of assay sensitivity (FIG. 7). Peripheral myeloid cells are the primary source of IL-1β and IL-18, with their ability to access the retina in AMD, we hypothesised that these cells would be key cells of interest in our system. Human peripheral blood mononuclear cells (PBMCs) produced IL-1β and IL-18 in response to activation with drusen even at very low concentrations (FIG. 1e,f). We used RPE material that was produced during the dissection of drusen from AMD eyes as a control for these experiments (FIG. 8). Immunoblot analysis of caspase-1 expression in THP-1 cell lysates post-treatment with drusen confirmed increased levels of cleaved caspase-1 p10 (FIG. 1g and FIG. 9). Together, these results demonstrate that drusen from AMD donor eyes can activate caspase-1 and the ASC inflammasome complex, which in turn results in IL-1β and IL-18 production in PBMCs.

We reasoned that NLRP3 was the likely sensor for drusen-induced inflammasome activation as it is required for inflammasome activation by particulate matter. We isolated bone marrow from both wild type (WT) and NLRP3-deficient (Nlrp3$^{-/-}$) mice and cultured bone marrow derived macrophages and dendritic cells (BMDMs and BMDCs). Both WT BMDMs and BMDCs produced significant levels of IL-1β in response to drusen, conversely Nlrp3$^{-/-}$ BMDMs and BMDCs (FIG. 1h,i, left panels) were unable to promote the production of mature IL-1β in response to drusen. Levels of IL-6 and TNFα were unaltered by the presence of drusen, indicative of a specific effect on IL-1β production (FIG. 1h,i right panels). These results demonstrate that AMD drusen are capable of activating the NLRP3 inflammasome.

CEP-Adducted Human Serum Albumin Primes the NLRP3 Inflammasome

Up to 65% of the proteins that have been identified in drusen were found in drusen isolated from both AMD and normal donors. However, oxidative protein modifications have also been observed in drusen, including carboxyethyl pyrrole protein adducts. Cumulative oxidative damage contributes to aging and has long been suspected of contributing to the pathogenesis of AMD (27, 28, 29). Carboxyethyl pyrrole (CEP) adducts are uniquely generated from the oxidation of docosahexaenoate (DHA)-containing lipids and are significantly more abundant on drusen and serum of AMD subjects (19). Recently, carboxyalkylpyrroles, among them CEP, have been shown to be recognized by Toll-like receptor 2 (TLR2) on endothelial cells (30). Given that TLR2 activation would prime cells to induce pro-IL-1β, pro-IL-18 and NLRP3 we hypothesised that CEP adducted proteins in drusen and on Bruch's membrane could present a novel priming agent.

Figure 2:
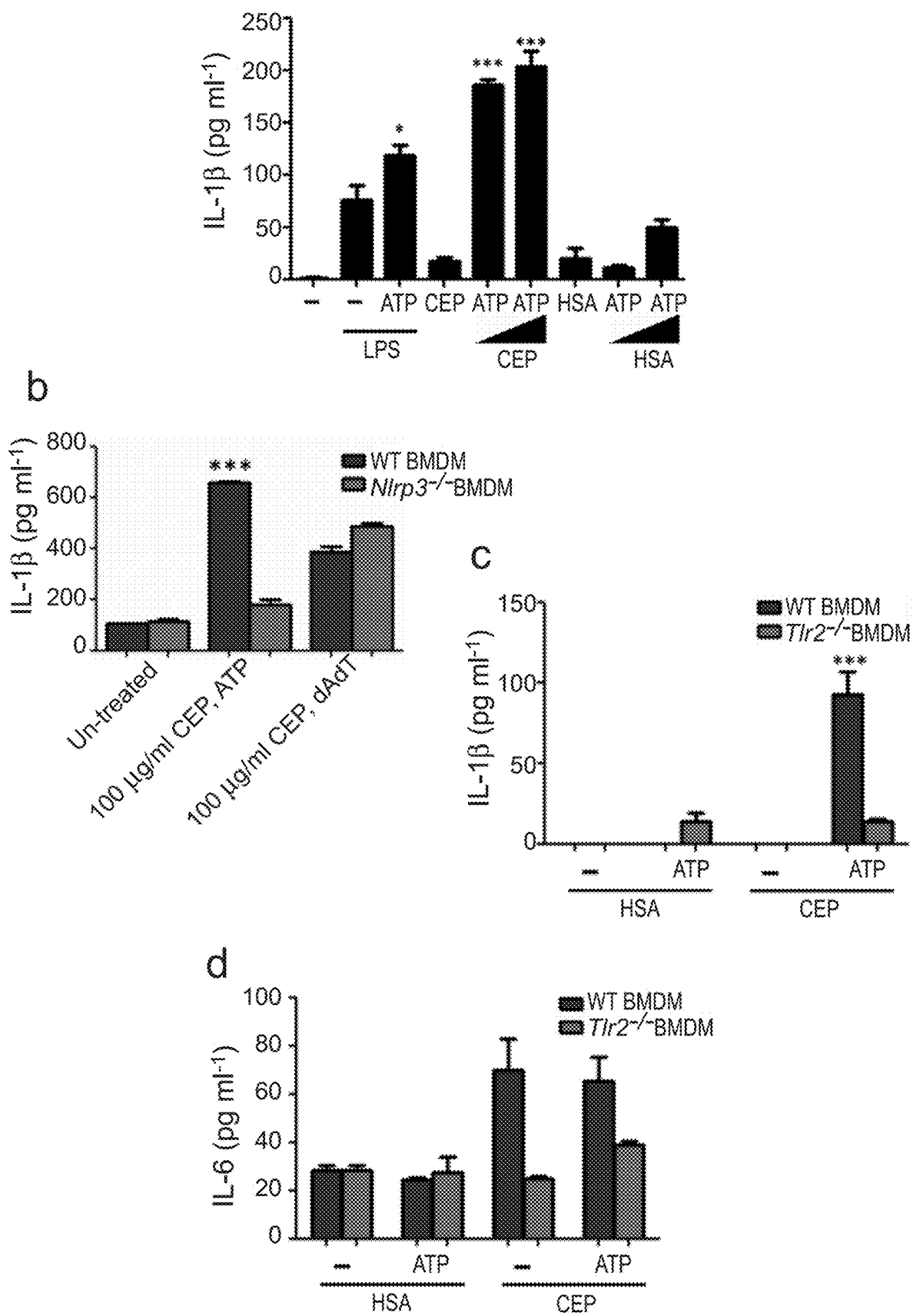
FIG. 2: CEP, a component of Drusen can prime the NLRP3 inflammasome: (a) Production of IL-1β in Human PBMC primed with LPS, CEP-adducted albumin (CEP-HSA) or HSA in increasing doses (50 and 100 µg ml$^{-1}$) and subsequently treated with 5 mM ATP. (b) IL-1β production in WT and Nlrp3$^{-/-}$ BMDMs primed with CEP-HSA and then activated with either ATP or Poly(dAdT). (c, d) IL-1β and IL-6 production in WT or Tlr2$^{-/-}$ BMDMs primed with HSA or CEP-HSA, activated with ATP or left un-treated. (e,f) IL-1β and TNFα production were measured in C3H/HeN BMDMs (WT) or C3H/HeJ BMDMs (which contain a mutant TLR4) primed with either LPS or CEP and activated with ATP. (g) Live cell imaging of immortalised BL6 BMDMs stably expressing YFP-ASC. Cells were primed for 3 h with CEP-HSA (top panel) or HSA (bottom panel) followed by treatment with 250 ng/ml Drusen for a further 2 hrs. Oligomerisation of ASC-YFP was observed by speck formation, original magnification ×60. All ELISA data are representative of a minimum of 3 separate experiments carried out in triplicate.
Figure 2:
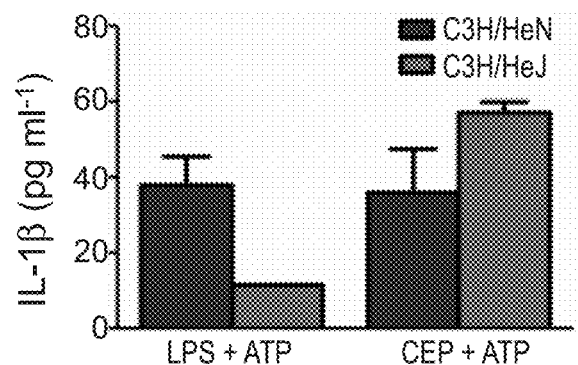
Figure 2:
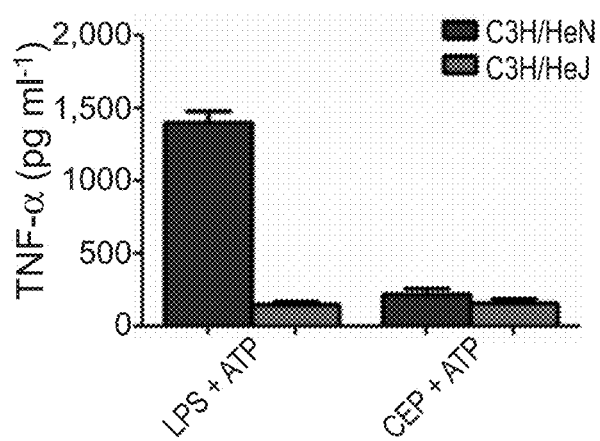
Figure 2:
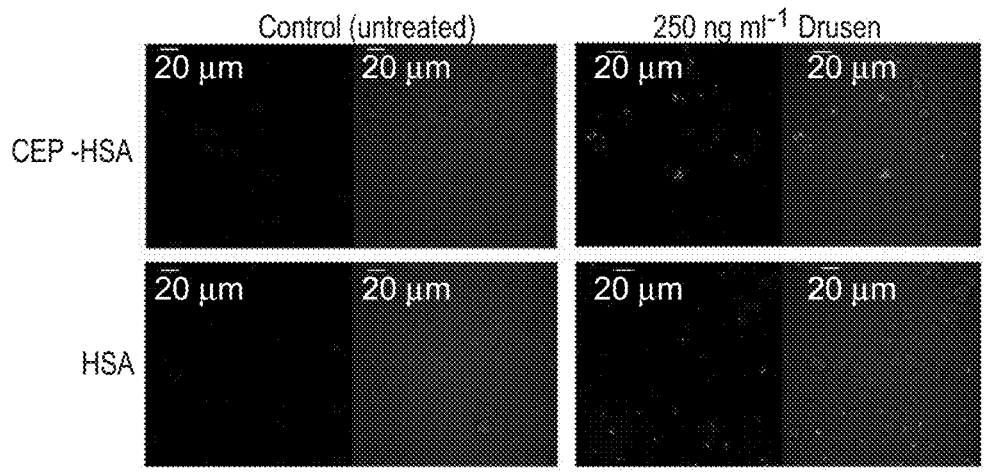
Figure 10:
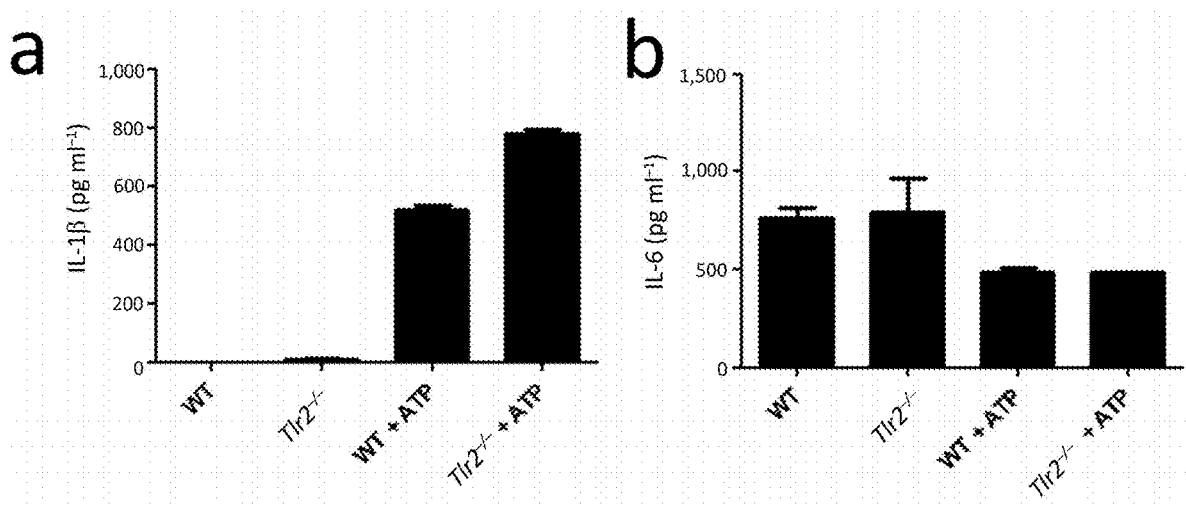
FIG. 10: a) IL-1β levels were significantly increased in LPS primed WT and Tlr2$^{-/-}$ BMDMs activated by ATP b) IL-6 levels were not significantly different.

To test this we primed PBMCs with increasing concentrations of CEP-adducted HSA or HSA alone and activated the cells with ATP. IL-1β levels increased with increased concentrations of CEP-HSA, but no changes were observed in cells primed with HSA alone (FIG. 1a). WT BMDMs primed with CEP-HSA and activated with ATP also produced IL-1β, an effect not observed in Nlrp3$^{-/-}$ mice (FIG. 2b). In order to ascertain whether CEP-HSA was priming the cells through TLR2 activation, we primed WT and TLR$^{-/-}$ BMDMs with HSA or CEP-HSA and activated with ATP. ATP activation induced IL-1β increases in WT but not TLR2$^{-/-}$ BMDMs primed with CEP-HSA. Furthermore, no IL-1β induction was observed in BMDMs primed with HSA prior to activation, again confirming that it is the CEP modification that infers the ability to activate TLR2 (FIG. 2c). IL-6 levels are equivalent between CEP-HSA treated WT cells, confirming the specificity of the response for IL-1β (FIG. 2d). IL-1β levels were measured in LPS primed WT and TLR2$^{-/-}$ BMDMs activated by ATP to ensure TLR2$^{-/-}$ BMDMs were responding optimally (FIG. 10). To ensure our CEP-HSA was not LPS contaminated we isolated BMDMs from C3H/HeN and C3H/HeJ mice. C3H/HeJ mice carry a mutation in their Tlr4 gene which renders them un-responsive to LPS (31). C3H/HeJ BMDMs produced IL-1β in response to ATP when primed with CEP-HSA but not LPS (FIG. 2e), indicating that our CEP adduct is LPS-free and primes the inflammasome through TLR2 ligation. TNF-α was detected in LPS primed WT C3H/HeN BMDMs but not CEP primed cells (FIG. 2f). We further examined the ability of CEP to prime the NLRP3 inflammasome by measuring ASC-YFP speck formation in CEP-treated BMDMs. Focused ASC-YFP specks were observed in BMDMs primed with CEP-HSA and activated with drusen (FIG. 2g, top panel). Drusen alone appeared to be able to cause the oligomerisation of ASC (FIG. 2g, bottom panel), implying that alone, drusen could initiate the formation of the multi-protein platform for inflammasome activation. However, we were unable to consistently detect IL-1β increases when PBMCs or BMDM/BMDCs were treated with drusen alone and assayed by ELISA.

Drusen Component Complement Factor C1Q, Activates the Inflammasome

Figure 3:
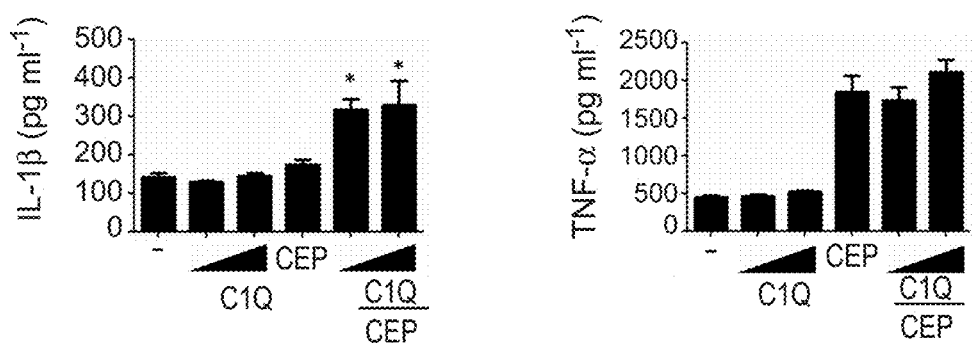
FIG. 3: Complement factor C1Q, a component of Drusen, activates the NLRP3 inflammasome: (a) Production of IL-1β (left panel) and TNFα (right panel) in BMDMs primed with CEP for 3 h and activated for 6 h with C1q at increasing doses. (b) Western blot of caspase-1 cleavage products in THP1 cells primed with LPS and treated with increasing doses of C1Q. (c) Live cell imaging of immortalised BL6 BMDMs stably expressing YFP-ASC. Cells were primed for 3 hrs with either LPS (top panel) or CEP-HSA followed by treatment with 10 μg ml$^{-/-}$ C1Q (right panel) for a further 2 hrs. Oligomerisation of ASC-YFP was observed by speck formation, original magnification ×60. (d) IL-1β (left panel) and TNF-α (right panel) production in WT and Nlrp3−/− BMDCs primed with LPS (3 h) and activated with C1Q (16 h) at increasing doses (2.5, 5 and 10 μg ml$^{-/-}$ C1Q). (e) IL-1β, IL-18 and IL-6 production in human PBMC primed with 100 ng ml$^{-/-}$ LPS overnight and activated with 5 μg ml$^{-/-}$ C1Q for 6 h, with the addition, 1 h before C1Q treatment of increasing doses (10 fold) of ZVAD (caspase-1 inhibitor). All ELISA data are representative of a minimum of 3 separate experiments carried out in triplicate.
Figure 3:
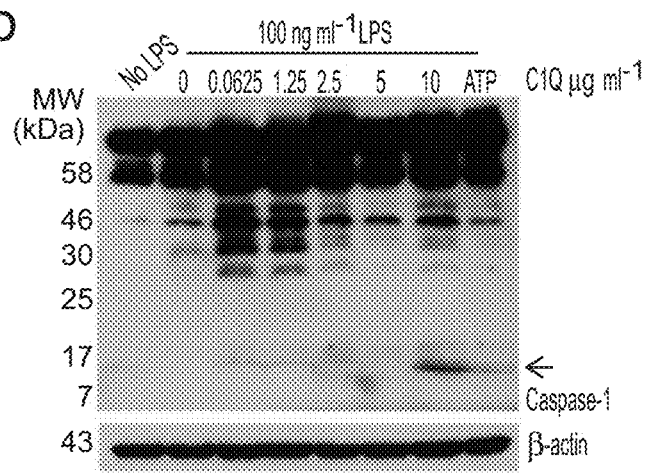
Figure 3:
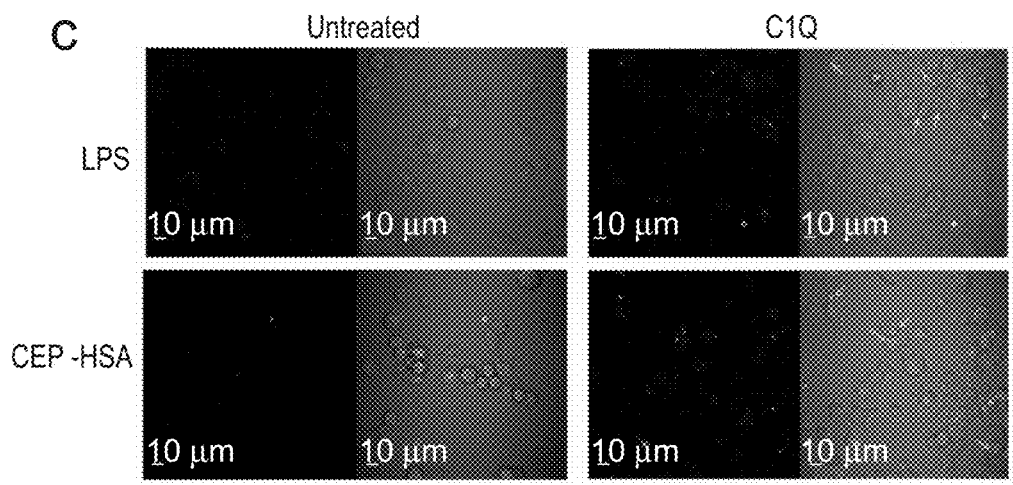
Figure 3:
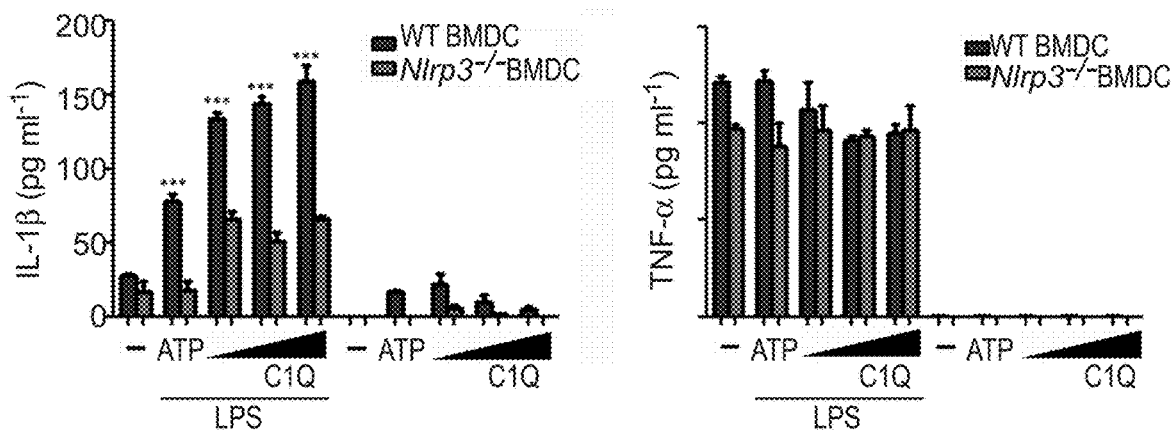
Figure 3:
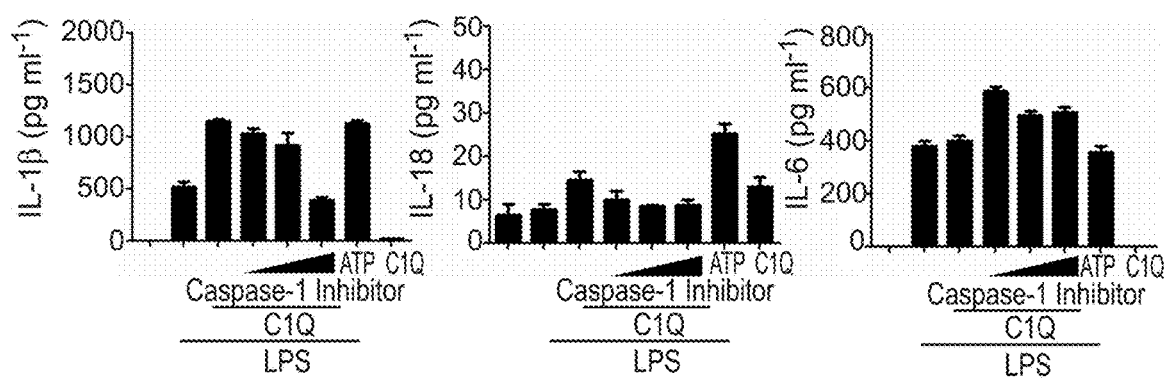
Figure 11:
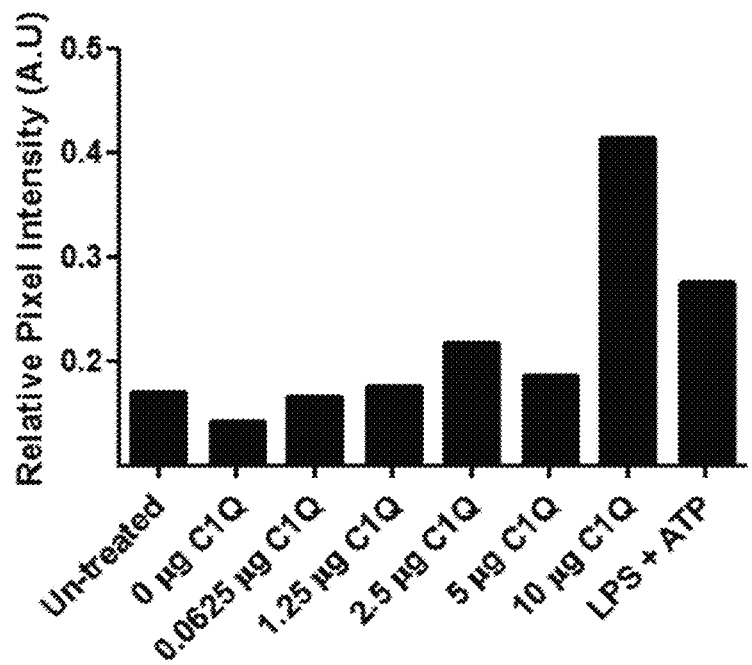
FIG. 11: Densitometric analysis of Caspase-1 P10 Western blot following treatment of THP1 cells with increasing doses of C1Q.

Although drusen can distort and eventually damage the retina as in GA (29), not all people presenting with drusen develop vision loss, therefore it is conceivable that in addition to the particulate nature of drusen causing mechanical insult to the RPE, some component(s) of drusen may be involved in the activation of the inflammasome in a more specific manner. We elected to study C1Q, the primary initiating component of the classical complement pathway, which has been identified in drusen (32). Since C1Q is an effector of the innate immune system with the potential to be extremely damaging to host tissue, its presence in drusen is indicative of an earlier or ongoing inflammatory insult. We directly evaluated the ability of C1Q to activate the NLRP3 inflammasome. Addition of C1Q alone to BMDMs did not cause the production of IL-1β, however cells that were primed with CEP-HSA before the addition of C1Q produced significant levels of IL-1β (FIG. 3a, left panel). Secretion of the pro-inflammatory cytokine TNFα remained unchanged upon addition of C1Q to CEP-HSA primed BMDMs (FIG. 3a, right panel), indicating that C1Q is specifically activating the inflammasome and is not involved in the up-regulation of pro-inflammatory cytokines in general. We observed cleaved caspase-1 p10 in THP1 human monocytic cells activated with C1Q (FIG. 3b, FIG. 11) and further established that C1Q could cause ASC oligomerisation as YFP-ASC specks can be seen in concentrated focal points within the cells activated with C1Q after priming with either LPS (FIG. 3c, top right-panel) or with CEP (FIG. 3c, bottom right-panel).

Figure 12:
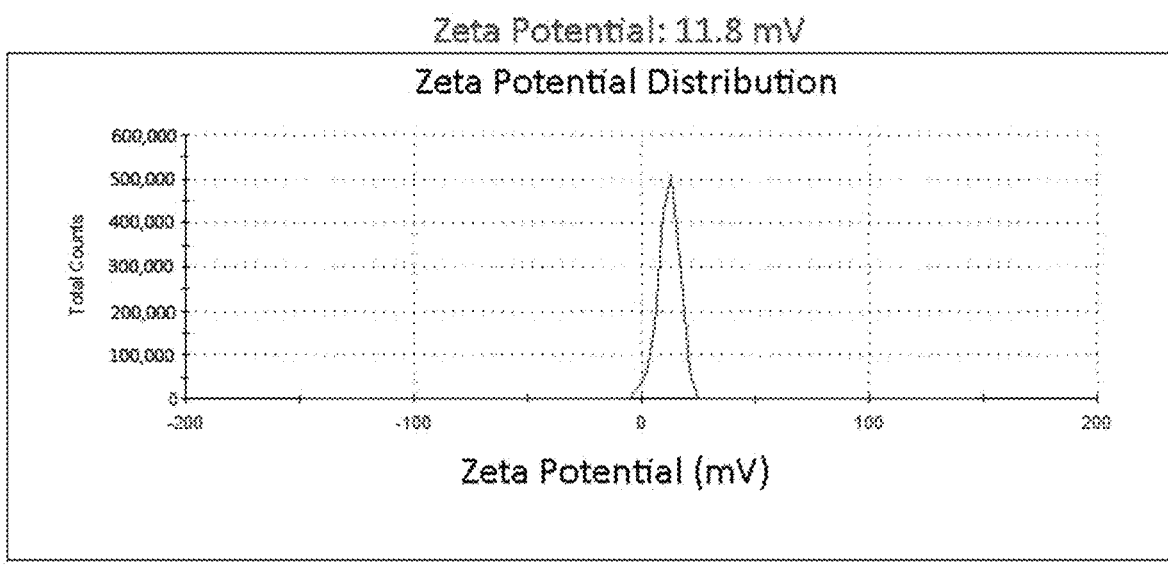
FIG. 12: Zeta potential measurement of C1Q in solution shows a zeta average of 11.8 mV.

WT BMDCs treated with C1Q did produce a significant level of IL-1β, however Nlrp3$^{-/-}$ BMDMs failed to produce IL-1β in response to C1Q activation (FIG. 3d, left), levels of TNFα remained unchanged (FIG. 3d, right). To confirm the role of caspase-1, we added a caspase-1 inhibitor, ZVAD, to human PBMC before C1Q activation. Caspase-1 inhibition decreased both IL-1β and IL-18 production in a dose dependent manner (FIG. 3e). Together these results show that C1Q can act as a danger signal sensed by the NLRP3 inflammasome. All C1Q isolated from human blood and C1Q found in drusen has a propensity to aggregate and we have shown this following zeta-potential analysis of a solution of C1Q, we believe this is a key factor in how C1Q can activate the NLRP3 inflammasome (FIG. 12)

C1Q Inflammasome Activation Involves the Phagolysosome

Figure 13:
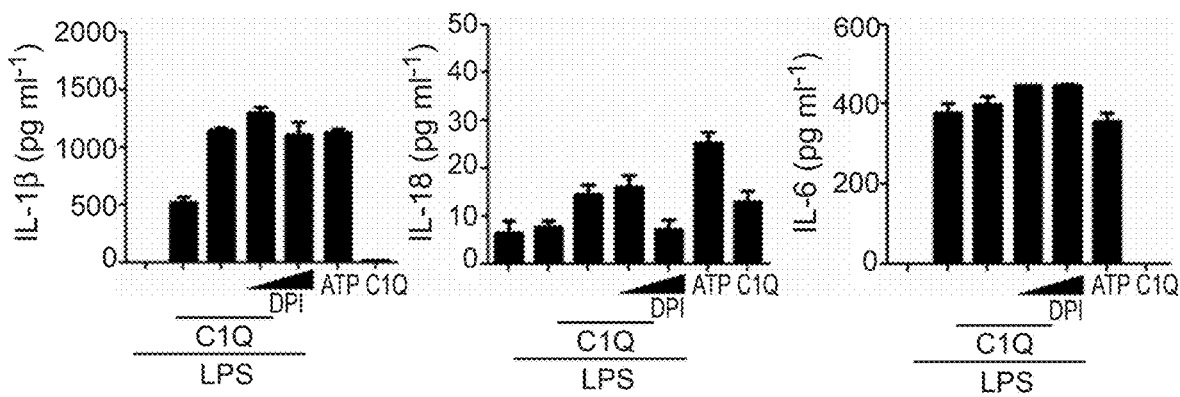
FIG. 13: IL-1β, IL-18 and IL-6 production in human PBMC primed with 100 ng/ml LPS overnight and activated with 5 μg/ml C1Q for 6 h, with the addition, 1 h before C1Q treatment of increasing doses (10 fold) of (a) DPI (ROS inhibitor), (b) Bafilomycin (inhibits lysosomal acidification), (c) CA-074 Me (cathepsin B inhibitor).
Figure 13:
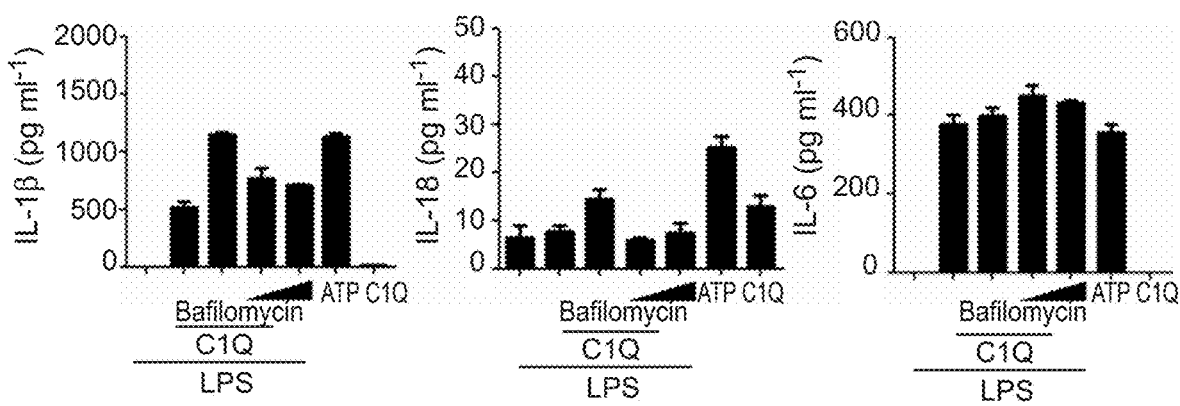
Figure 13:
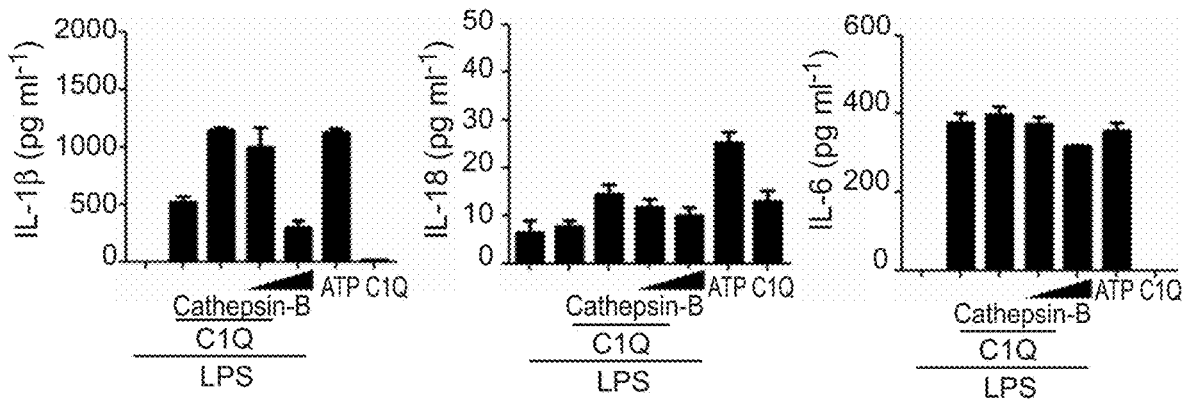

Deposits of C1Q along with other complement factors have been shown to be associated with, or components of, amyloid structures (33, 34). It is therefore likely that C1Q as a component of drusen would result in its aggregation and assist macrophages as they attempt to phagocytose these particulate deposits. The mechanisms leading to NLRP3 inflammasome activation are still a matter of debate and may depend on the stimulus. One mechanism involves the phagocytosis of particulate structures leading to lysosomal rupture and release of lysosomal contents (35). Another proposed mechanism involves the production of reactive oxygen species (ROS) which lead to the activation of the NLRP3 inflammasome via ROS-sensitive TXNIP protein (36). To determine if C1Q induction of ROS (37,38) was responsible for inflammasome activation we treated PBMC with the NADPH oxidase inhibitor DPI prior to C1C2 activation. Inhibition of ROS by DPI had no effect on C1Q induced IL-1β release (FIG. 13a). The alternative mechanism proposed is that lysosomal instability leads to the leakage of the lysosomal-exopeptidase, cathepsin B, into the cytosol which is sensed by the components of the inflammasome leading to its assembly (35). To determine the role of the phagolysosome in the activation of the inflammasome by C1Q we used bafilomycin A, an inhibitor that blocks the vacuolar H$^+$ ATPase system necessary for lysosomal acidification and the cathepsin B inhibitor CA-074 Me. Inhibition of either vacuolar ATPase or cathepsin B restricted C1Q activated production of IL-1β and IL-18 with no effect on IL-6 production (FIG. 13b, c). This directly implies that C1Q alters the phagolysosomal process to trigger NLRP3 activation.

NLRP3 Inflammasome is Active in CEP-MSA Immunized Mice

Figure 4:
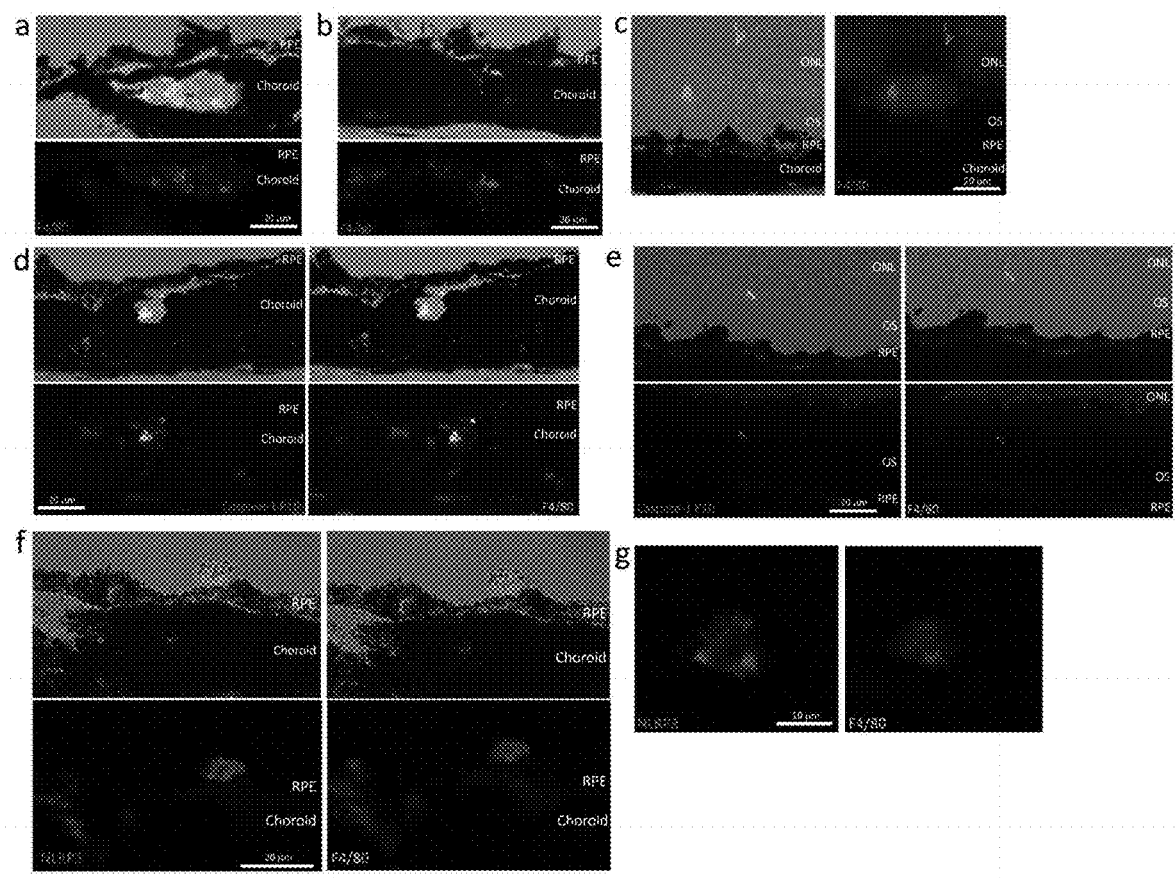
FIG. 4: Cleaved caspase-1 p10 co-localizes with activated macrophages in CEP-MSA immunized mice: (a-c) Immunostaining of retinal cryosections of CEP-MSA immunized mice showing localisation of F4/80 positive macrophages (a) to regions of the choroid (b) extending from the choroid towards Bruch's membrane and (c) present above the RPE in the outer segments (OS) and outer nuclear layer (ONL) of the retina. (a,b) Top panel (c) left-hand panel, differential interference contrast (DIC) image, (a,b) bottom panel (c) right-hand panel, fluorescent image (F4/80-red, DAPI-blue). (d,e) Co-labelling of retinal cryosections of CEP-MSA immunized mice with caspase-1 p10 (red) and F4/80 (green) showing co-localisation in (d) a macrophage present within and transcending the choroid/Bruch's membrane and (e) a macrophage protrusion in the OS of the retina. (f) Co-labelling of retinal cryosections of CEP-MSA immunized mice show co-localisation of NLRP3 (red) and F4/80 (green). (g) High magnification of NLRP3 and F4/80 staining.
Figure 14:
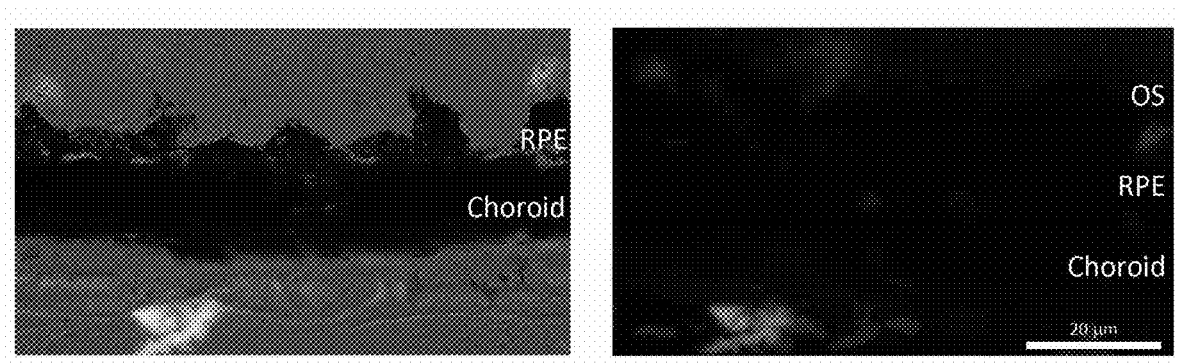
FIG. 14: CD68 staining (red) in a CEP-MSA immunized mouse retina, showed positive cells in the sclera and outer segments (OS) of the retina.
Figure 15:
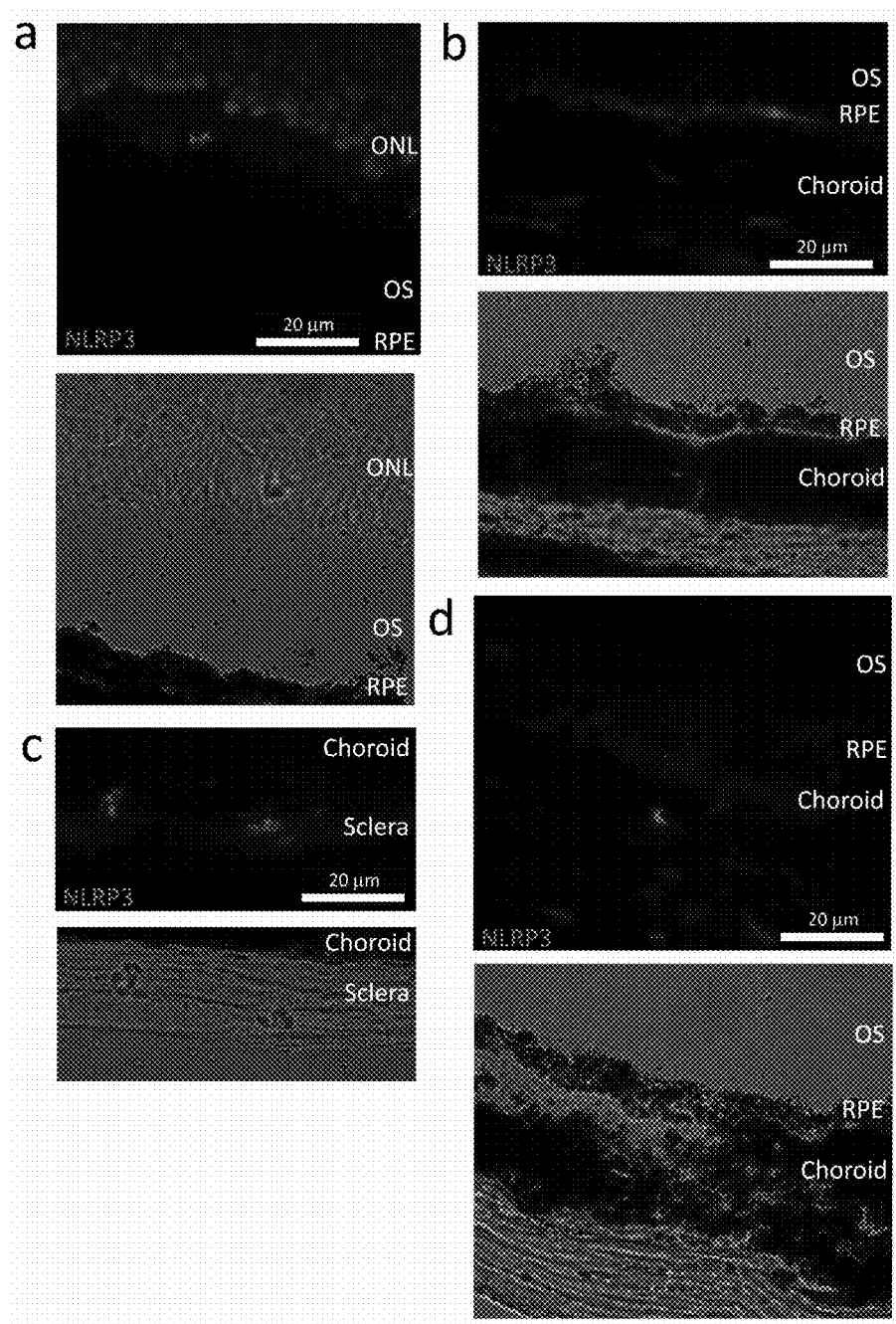
FIG. 15: CEP-MSA immunized mouse retinal cryosections were stained for NLRP3 and positive immunoreactivity was observed in the (a) outer segments of the retina, (b) retinal pigment epithelium (RPE), (c) cells within the sclera and (d) cells within the choroid.

We sought to determine whether the inflammasome was involved in the pathology of a well characterised model of dry AMD, the CEP-MSA immunised mouse model. This animal develops AMD-like lesions in its retina and RPE following immunization with CEP-MSA. We analysed retinal sections of CEP-MSA immunized mice, for the presence of activated macrophages (F4/80 and CD68 staining), caspase-1 p10 and NLRP3. Activated macrophages were observed to be present within the choroid and Bruch's membrane (FIG. 4a,b, FIG. 14), We also observed infiltrating macrophages above the RPE in the outer segments of the retina (FIG. 4c). Staining of these sections showed co-localisation of F4/80 with cleaved caspase-1 p10 (FIG. 4d,e) and NLRP3 (FIG. 4f,g, FIG. 15).

NLRP3 Protects Against Exacerbated Laser-Induced CNV Development

Figure 5:
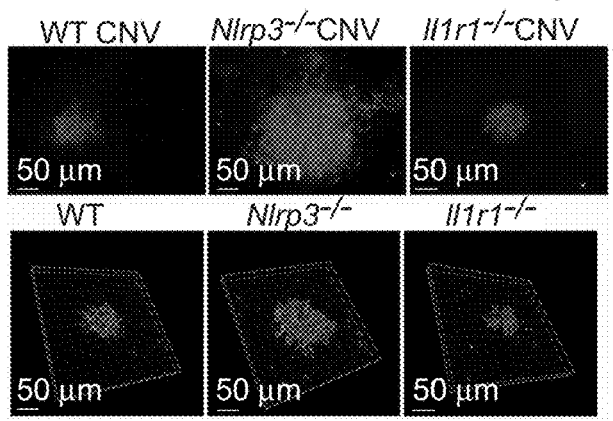
FIG. 5: NLRP3 is protective against laser-induced CNV lesion formation in an IL-1β independent manner: (a) Laser induced CNV in WT (top left panel), Nlrp3$^{-/-}$ (top middle panel) and Il1r1$^{-/-}$ (top right panel) mice showing CNV development 6 days post laser burn. 3-D re-constructed images of confocal Z-stacks from WT (bottom left panel), Nlrp3$^{-/-}$ (bottom middle panel) and Il1r1$^{-/-}$ (bottom right panel). CNV volume rendering (Bar chart). (b) Electroretinographic (ERG) analysis of rod and cone function of Nlrp3$^{-/-}$ and Il1r1$^{-/-}$ mice. (c) Immunostaining showing localization of activated macrophages (F4/80-green) to the site of laser induced injury in Nlrp3$^{-/-}$ mice. (d) Immunostaining of WT (left hand panel) or Nlrp3$^{-/-}$ (right hand panel) retinal cryosections 3 hours post injury, for cleaved caspase-1 (red).
Figure 5:
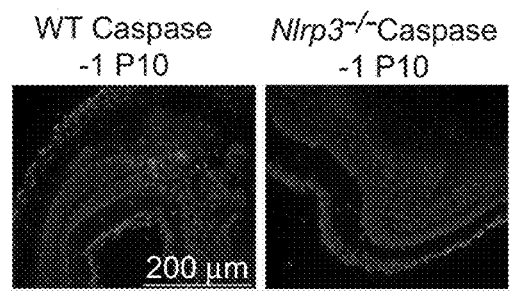
Figure 5:
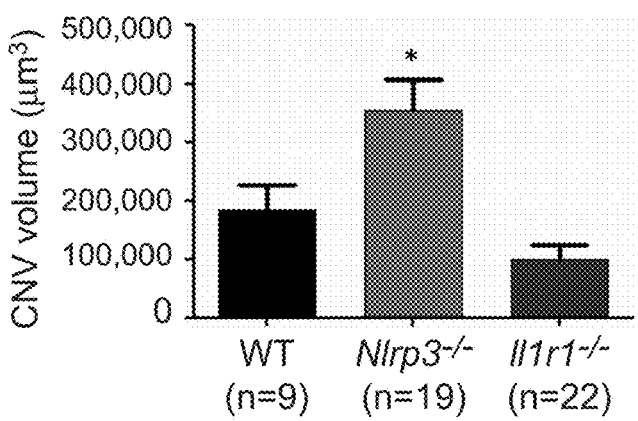
Figure 5:
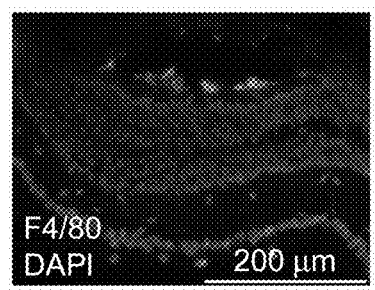
Figure 5:
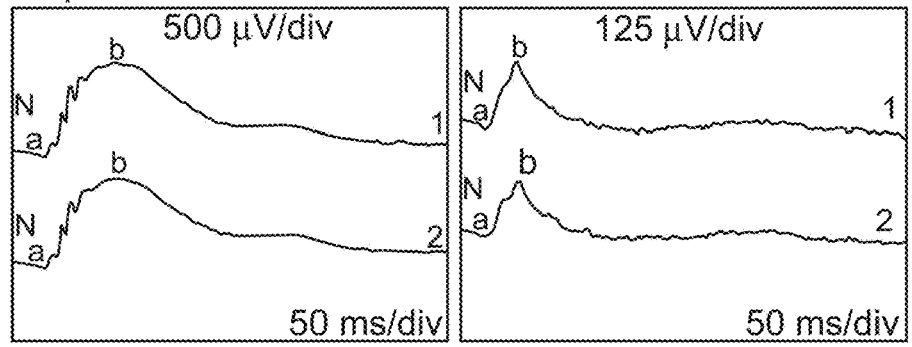
Figure 5:
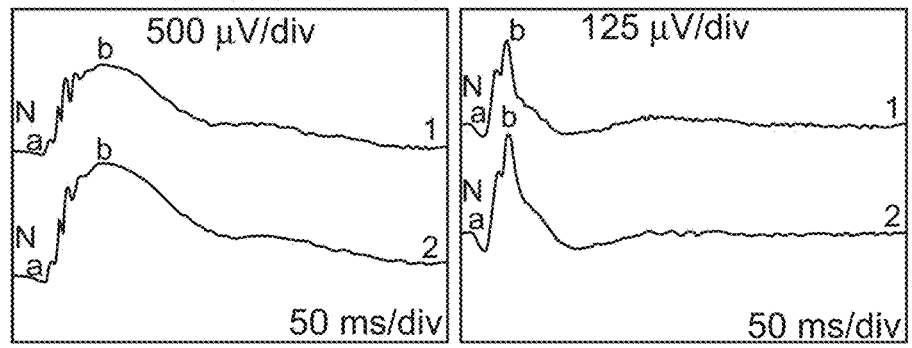
Figure 16:
FIG. 16: F4/80 (left panel, red) and caspase-1 p10 (middle panel, green) co-localized to the site of laser induced CNV in WT mice (right panel)
Figure 17:
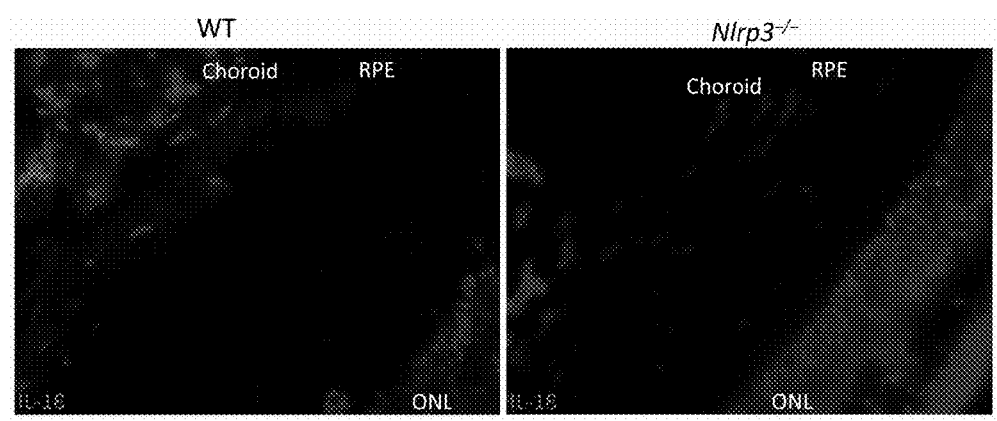
FIG. 17: IL-18 was observed in at the site of laser induced injury in WT mice 24 h post injury (left panel-red staining). This staining was not evident at the site of injury in Nlrp3$^{-/-}$ mice (right panel-red staining).

A much used model for wet (exudative) AMD is laser induced CNV, which is also an ideal model for sterile inflammation (39), likely due to the induction of a necrotic microenvironment within the tissue. Necrotic cells are known to trigger a sterile inflammatory response through the NLRP3 inflammasome (17). We hypothesised that the NLRP3 inflammasome may play a key role in CNV development in response to localised tissue injury. In order to test our hypothesis we administered focal laser burns to the retinas of WT, Nlrp3$^{-/-}$ and Il1r1$^{-/-}$ mice and assessed CNV volumes. Surprisingly we found significantly more CNV development and sub-retinal haemorrhaging in Nlrp3$^{-/-}$ mice when compared with WT and Il1r1$^{-/-}$ mice (FIG. 5a). 3D Z-stack confocal volume rendering of CNVs confirmed a significant increase in CNV volume in Nlrp3$^{-/-}$ mice 6 days post injury (FIG. 5d, histogram). Electroretinographic (ERG) analysis confirmed both knockout mice have functional rod and cone responses pre-injury (FIG. 5b). We observed activated macrophage infiltration (positive F4/80 immunoreactivity) at the lesion site in Nlrp3$^{-/-}$ mice (FIG. 5c), however, cleaved caspase-1 and IL-18 were only evident at the injury site of WT mice and were notably absent in Nlrp3$^{-/-}$ mice (FIG. 5d, FIG. 16, 17). These findings describe a role for the NLRP3 inflammasome in the sterile inflammatory response observed in this animal model of CNV and point towards IL-18 as a regulator of CNV development.

NLRP3 Confers Protection Against CNV Lesion Formation Through IL-18

Figure 6:
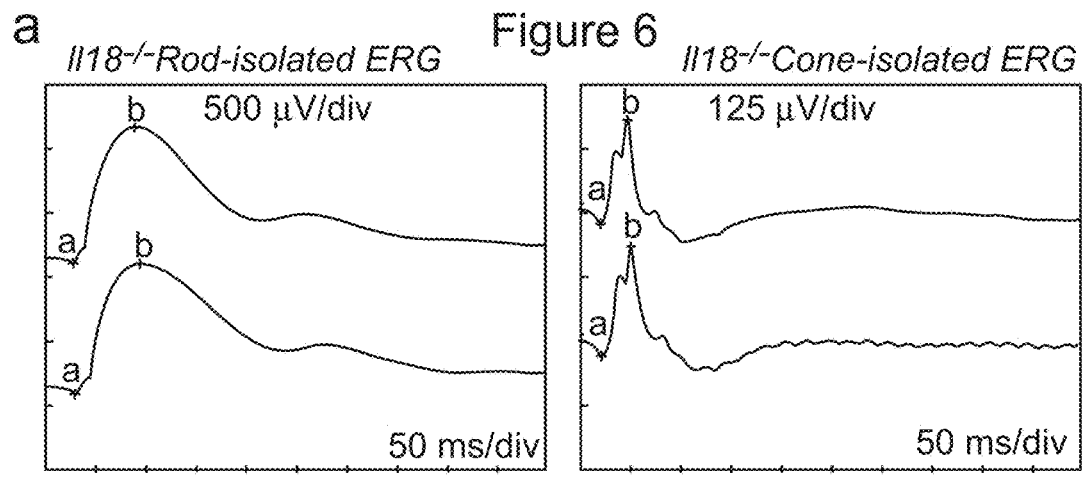
FIG. 6: NLRP3 confers its protection against CNV lesion formation through its role in IL-18 production, which in turn regulates VEGF levels: (a) Electroretinographic (ERG) analysis of rod and cone function of Il18$^{-/-}$ mice. (b) Laser induced CNV in Il18$^{-/-}$ mice showing CNV development 6 days post laser burn (left hand panel). 3-D re-constructed images of confocal Z-stacks (right hand panel). CNV volume rendering (Bar chart). (c) CNV volumes were significantly increased compared to WT mice (FIG. 5) (*P=0.0292). The production of VEGF was assayed by ELISA in (d) ARPE-19 cells and (e) Mouse brain microvascular endothelial cells (B.end3) treated with increasing doses of IL-18 for 24 hrs or left untreated. ELISA data are representative of a minimum of 3 separate experiments carried out in triplicate.
Figure 6:
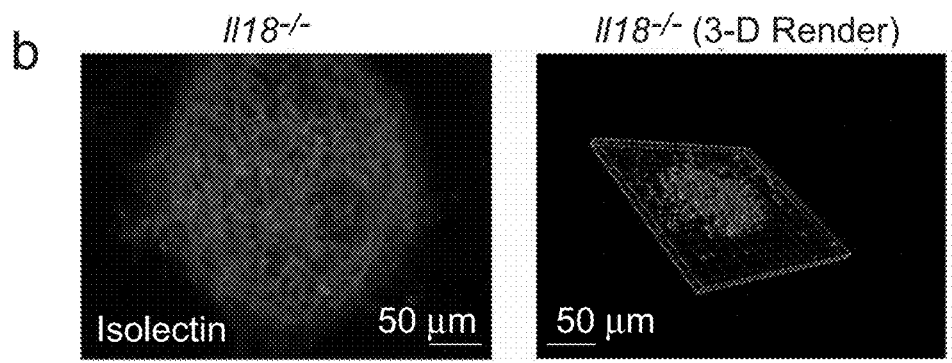
Figure 6:
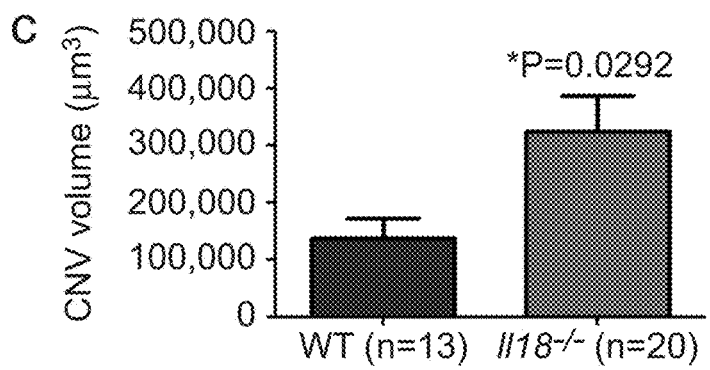
Figure 6:
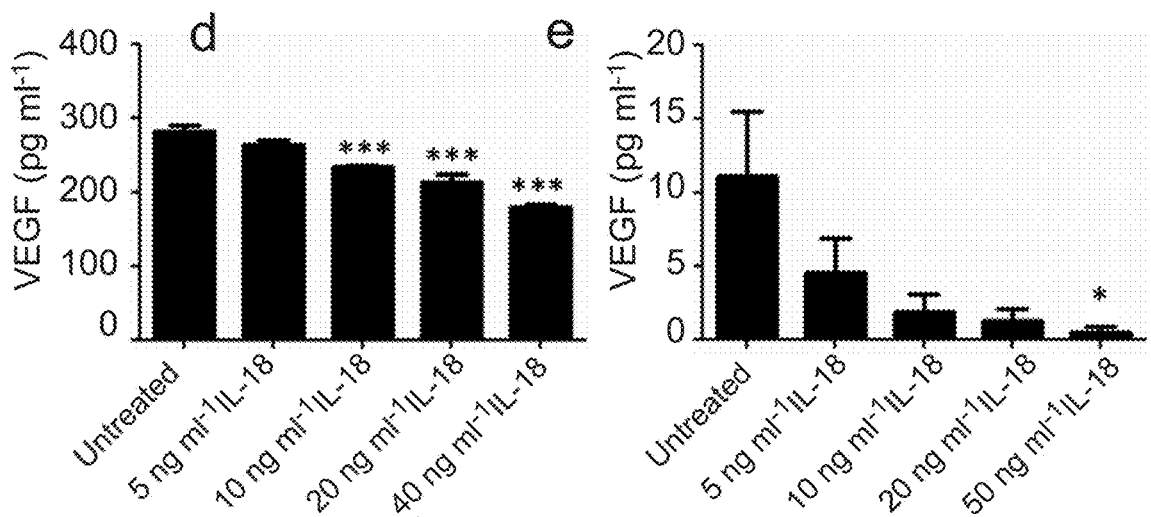
Figure 18:
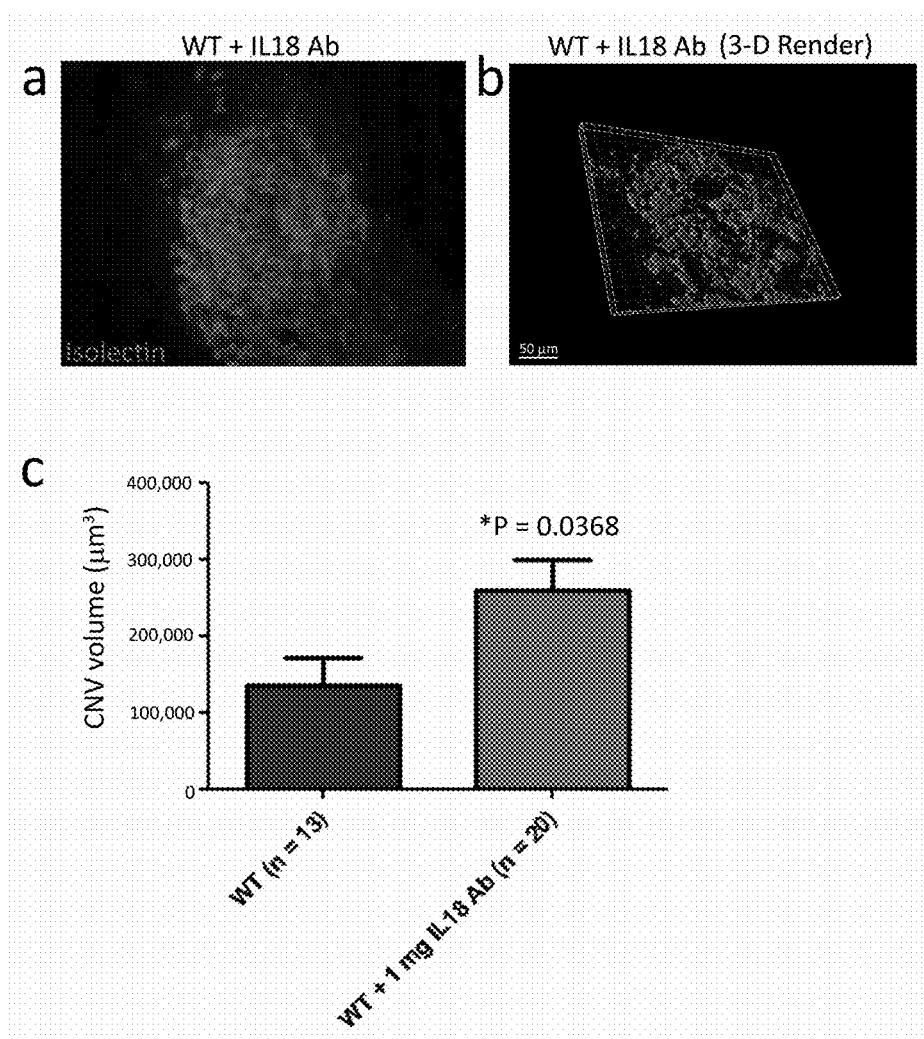
FIG. 18 (a) Neutralizing IL-18 (1 μg) antibody injected post laser induced CNV significantly increased CNV size in WT mice as measured by epifluorescent microscopy, (b) Confocal, Z-stack 3-D rendered image of CNV. (c) Significantly increased CNV's were observed in WT mice injected with 1 μg IL-18 neutralizing antibody post laser injury compared to sham injected mice (*P=0.0368).

In order to confirm a role for IL-18 in NLRP3-mediated protection against exacerbated CNV development, we administered laser induced CNVs in IL18$^{-/-}$ mice. These mice were observed to have normal retinal function (FIG. 6a) as assessed by ERG analysis. Laser induced disruption of Bruch's membrane and CNV volume quantification in IL18$^{-/-}$ mice 6 days post injury showed markedly increased lesions (FIG. 6b) compared to WT CNVs (FIG. 6c). Intravitreally injected IL-18 neutralising antibodies subsequent to laser induced CNV also resulted in significantly increased CNV development (FIG. 18).

We reasoned that IL-18 might confer its protection via the regulation of VEGF synthesis. To test this hypothesis we treated ARPE19 cells and a mouse brain microvascular endothelial cell line (bEnd.3) with recombinant IL-18 and subsequently analysed VEGF levels in the growth medium. IL-18 significantly decreased levels of VEGF secreted by both ARPE-19 cells and bEnd.3 cells (FIG. 6d,e). These findings directly implicate a role for IL-18 in the regulation of VEGF expression and likely explain the exacerbated CNVs in Nlrp3$^{-/-}$ and/L/8$^{-/-}$ mice.

CONCLUSION

Our studies have shown that drusen isolated from AMD donor eyes can activate the NLRP3 inflammasome. Furthermore, we show that carboxyethyl-pyrrole (CEP), an oxidative stress related protein modification commonly found decorating drusen proteins, can prime the inflammasome. In tandem, we show that the complement component C1Q can activate the NLRP3 inflammasome in a caspase-1 and phagolysosome dependent manner. We observed activated caspase-1 and NLRP3 in macrophages surrounding the drusen-like lesions associated with CEP-MSA immunised mice, an accepted model of dry AMD. We also found that a commonly used animal model of wet AMD, is dependent on NLRP3 activation, but unexpectedly in the absence of NLRP3, CNV development was exacerbated. We implicate IL-18 as a key regulator of pathological neovascularisation and suggest a protective role for the NLRP3 inflammasome in the development of AMD.

Our observations have major implications in regard to prevention of AMD. Current antibody-based therapies target advanced forms of AMD by inhibiting the bioactivity of VEGF. However, direct and regular intraocular injection of these monoclonal antibodies (Lucentis® and Avastin®) carry the risk of retinal detachment, haemorrhage and infection.

We have shown that drusen isolated from AMD donor eyes can activate the NLRP3 inflammasome. AMD drusen is composed of a collection of protein deposits, many of which are adducted to CEP. Due to its particulate nature, it is possible that drusen from normal donor eyes may also induce inflammasome activation, however it's levels in the retina by definition, are lower than AMD drusen and the biochemical compositions are different. These differences are likely important for the progression of AMD. A comparison of control and AMD drusen in relation to inflammasome activation has, however, yet to be fully elucidated.

We have demonstrated that CEP-HSA can prime the inflammasome through TLR2 activation providing us with a naturally occurring priming agent that accumulates at focal points at high levels within the AMD eye. In the case of NLRP3, the danger signal is usually particulate and extracellular in nature. C1Q, a component of drusen, has been shown to aggregate in an amyloid-like fashion. We show that C1Q, isolated from human blood, activates the NLRP3 inflammasome in a manner dependent on lysosomal acidification and cathepsin B.

The sterile inflammatory response that occurs in AMD is likely a result of the focal necrosis that occurs in the RPE cells sub-adjacent to excessive drusen accumulation. Drusen accumulation in Bruch's membrane is a hallmark feature and diagnostic indicator of early AMD development and is thought to be central to the pathology of the disease. While we have observed inflammasome activation in macrophages associated with AMD-like lesions in CEP-MSA immunised mice, our observations for the first time directly indicate a protective role for inflammatory processes in the progression to CNV, the exudative form of AMD, and directly oppose current dogma directed at suppression of inflammatory processes in disease prevention. Indeed it is now accepted that some level of inflammation, "pare-inflammation", may be beneficial to the host. From a clinical perspective, while inflammatory processes have long been associated with AMD pathology and disease development, we suggest that global inhibition of inflammation in the retina in the case of wet AMD would not be a sound therapy. Lending strength to our observations, the results of recent clinical trials of Infliximab (Remicade®) in individuals with wet AMD showed that in more than 50% of these subjects, symptoms were greatly exacerbated.

The NLRP3 inflammasome has also recently been shown to confer protection, through IL-18 production, against experimental colitis and colorectal cancer in mice.

Previous studies indicate that IL-18 plays an important role in retinal vascular development. Il-18$^{-/-}$ mice showed angiectasis and vascular leakage, VEGF and bFGF levels were also up-regulated in the Il-18$^{-/-}$ mouse retinas. Anti-angiogenic roles for IL-18 have also been observed in post-ischemic injury and in the inhibition of tumour angiogenesis.

Activation of the NLRP3 inflammasome by drusen suggest that a balance may exist, whereby a certain focal level of drusen is tolerated due to its ability to induce IL-18 which in turn may act as an anti-angiogenic effector, maintaining choroidal homeostasis in an inflammatory micro-environment. It is likely that once a critical level of drusen accumulates, its protective role is negated by excessive damage to the surrounding tissues. Importantly, we have demonstrated that drusen-inducible inflammatory mediators are protective against CNV development and that it is the resultant NLRP3 mediated elevation of IL-18 that prevents the downstream production of VEGF. Moreover, IL-18 has been shown not to play a role in the development of experimental uveitis, a more conventional model of inflammation, a finding which has direct implications for future forms of therapy deriving from our findings. Overall, our observations directly implicate NLRP3 as a protective agent against the major disease pathology of AMD and suggest that strategies aimed at producing or delivering IL-18 to the eye, may prove beneficial in preventing the progression of CNV in the context of wet AMD.

Supplementary Methods
Clinical Evaluation

AMD subjects and un-affected individuals were assessed by a clinical ophthalmologist following informed consent. Best-corrected distance visual acuity was measured using a Snellen Chart. Near vision was assessed using Standard Test Type. The anterior segment of the eye was examined by slit-lamp biomicroscopy. Intraocular pressure was measured by Goldmann Tonometry. Detailed funduscopic examination and colour fundus photography were carried out following pupillary dilation using Tropicamide (1%). Dry AMD was diagnosed by the presence of visual distortion due to AMD-associated macular changes (drusen, hyperpigmentation, hypopigmentation of the RPE or geographic atrophy). Wet AMD was diagnosed by clinical examination supplemented by fluorescein angiographic photography to illustrate CNV.

ERG Analysis of Mice

Mice were dark-adapted overnight and prepared for electroretinography under dim red light. Pupillary dilation was carried out by instillation of 1% cyclopentalate and 2.5% phenylephrine. Animals were anesthetized by intraperitoneal (I.P.) injection of ketamine (2.08 mg per 15 g body weight) and xylazine (0.21 mg per 15 g body weight). Standardised flashes of light were presented to the mouse in a Ganzfeld bowl to ensure uniform retinal illumination. The ERG responses were recorded simultaneously from both eyes by means of gold wire electrodes (Roland Consulting Gmbh) using Vidisic (Dr Mann Pharma, Germany) as a conducting agent and to maintain corneal hydration. Reference and ground electrodes were positioned subcutaneously, approximately 1 mm from the temporal canthus and anterior to the tail respectively. Body temperature was maintained at 37° C. using a heating device controlled by a rectal temperature probe. Responses were analysed using a RetiScan RetiPort electrophysiology unit (Roland Consulting Gmbh). The protocol was based on that approved by the International Clinical Standards Committee for human electroretinography. Cone-isolated responses were recorded using a white flash of intensity 3 candelas/m$^{-2}$/s presented against a rod-suppressing background light of 30 candelas/m$^{-2}$ to which the previously dark adapted animal has been exposed for 10 minutes prior to stimulation. The responses to 48 individual flashes, presented at a frequency of 0.5 Hz, were computer averaged. Following the standard convention, a-waves were measured from the baseline to a-wave trough and b-waves from the a-wave trough to the b-wave peak.

The invention is not limited to the embodiment(s) described herein but can be amended or modified without departing from the scope of the present invention.

The invention claimed is:

1. A method of treating age-related macular degeneration comprising administering a therapeutically effective amount of recombinant human interleukin-18 (rIL-18) to a subject in need thereof.

2. The method according to claim 1 wherein the recombinant human rIL-18 is delivered systemically to said subject.

3. The method according to claim 1 wherein the recombinant human rIL-18 is delivered locally to said subject.

4. The method according to claim 1, wherein the age-related macular degeneration is wet age-related macular degeneration.

5. The method according to claim 1, wherein the recombinant human Interleukin-18 (rIL-18) is delivered to at least one eye, retina, and/or choroid of said subject.

6. The method according to claim 1, wherein the recombinant human Interleukin-18 (rIL-18) is delivered locally to at least one retina of said subject.

7. The method according to claim 1, wherein the recombinant human Interleukin-18 (rIL-18) is delivered to at least one retina of said subject by adeno-associated viral (AAV) mediated delivery.

8. The method according to claim 6, wherein the rIL-18 controls and/or suppresses choroidal neo-vascularisation (CNV).

9. The method according to claim 1 wherein the age-related macular degeneration is selected from wet or dry age-related macular degeneration.

10. The method according to claim 3, wherein the local delivery is selected from intraocular injection, sub-retinal injection, intra-vitreal injection, retrobulbar injection, sub-conjunctival injection and/or subtenon injection.

11. The method according to claim 1, wherein the recombinant human Interleukin-18 (rIL-18) is delivered to at least one retina of said subject by an adeno-associated virus (AAV) expressing an inducible rIL-18.

12. The method according to claim 1, wherein the recombinant human interleukin-18 prevents the production of VEGF.

13. A method of treating age-related macular degeneration comprising administering a composition consisting essentially of recombinant human interleukin-18 (rIL-18) to a subject in need thereof.

* * * * *